(12) United States Patent
Imran

(10) Patent No.: US 9,820,746 B2
(45) Date of Patent: Nov. 21, 2017

(54) SYSTEM AND METHOD FOR SCAFFOLDING ANASTOMOSES

(75) Inventor: Mir A. Imran, Los Altos Hills, CA (US)

(73) Assignee: Incube Laboratories LLC, San Jose, CA (US)

( * ) Notice: Subject to any disclaimer, the term of this patent is extended or adjusted under 35 U.S.C. 154(b) by 419 days.

(21) Appl. No.: 12/181,244

(22) Filed: Jul. 28, 2008

(65) Prior Publication Data

US 2010/0023132 A1    Jan. 28, 2010

(51) Int. Cl.
*A61F 2/02* (2006.01)
*A61B 17/08* (2006.01)
(Continued)

(52) U.S. Cl.
CPC .......... *A61B 17/1114* (2013.01); *A61B 17/11* (2013.01); *A61F 2/04* (2013.01);
(Continued)

(58) Field of Classification Search
CPC ............ A61F 2002/91525; A61F 2/848; A61F 2002/072; A61F 2002/8486;
(Continued)

(56) References Cited

U.S. PATENT DOCUMENTS 3,221,746 A * 12/1965 Noble ........................... 606/155
4,790,313 A 12/1988 Borrelly
(Continued)

FOREIGN PATENT DOCUMENTS

CN  2768714 Y  7/2003
JP  2005529193  9/2002
(Continued)

OTHER PUBLICATIONS

International Search Report and Written Opinion and Notice Thereof dated Mar. 15, 2010 for International Application No. PCT/US2009/051986 13 pages.
(Continued)

*Primary Examiner* — Jing Ou
(74) *Attorney, Agent, or Firm* — Mahamedi IP Law LLP; Joel Harris

(57) ABSTRACT

Embodiments of the invention provide systems and methods for using a tissue scaffold to facilitate healing of an anastomosis. One embodiment provides a tissue scaffold for placement at an anastomotic site within a body lumen comprising a radially expandable scaffold structure having lateral and mid portions, at least one retention element coupled to each lateral portion and a barrier layer. The retention element engages a luminal wall when the scaffold structure is expanded to retain the structure and exert a compressive force on the anastomosis. The mid portion has a greater radial stiffness than the lateral portions such that when the structure is expanded, the lateral portions engage tissue prior to the mid portion. The barrier layer is configured to engage a luminal wall when the structure is expanded to provide a fluidic seal at the anastomosis. The barrier layer may also include releasable biological agents to promote anastomotic healing.

18 Claims, 14 Drawing Sheets

(51) Int. Cl.

| | | |
|---|---|---|
| *A61B 17/11* | (2006.01) | |
| *A61F 2/06* | (2013.01) | |
| *A61F 2/04* | (2013.01) | |
| *A61F 2/848* | (2013.01) | |
| *A61F 2/07* | (2013.01) | |
| *A61B 17/00* | (2006.01) | |
| *A61B 90/00* | (2016.01) | |

(52) U.S. Cl.
 CPC .............. *A61F 2/064* (2013.01); *A61B 90/39* (2016.02); *A61B 2017/00004* (2013.01); *A61B 2017/00893* (2013.01); *A61B 2017/1103* (2013.01); *A61B 2017/1107* (2013.01); *A61B 2017/1117* (2013.01); *A61B 2017/1132* (2013.01); *A61B 2017/1135* (2013.01); *A61B 2017/1139* (2013.01); *A61B 2090/0807* (2016.02); *A61F 2/848* (2013.01); *A61F 2002/044* (2013.01); *A61F 2002/072* (2013.01); *A61F 2002/8483* (2013.01); *A61F 2002/8486* (2013.01); *A61F 2210/0004* (2013.01); *A61F 2250/0018* (2013.01); *A61F 2250/0069* (2013.01)

(58) Field of Classification Search
 CPC .... A61F 2002/8483; A61F 2/04; A61F 2/064; A61F 2250/0069; A61F 2210/0004; A61F 2250/0018; A61F 2002/044; A61B 2017/1132; A61B 2017/1117; A61B 17/1114; A61B 2017/1107; A61B 2017/1103; A61B 90/39; A61B 2090/0807; A61B 2017/0893; A61B 2017/1135; A61B 2017/00004; A61B 2017/1139
 USPC ....... 606/151, 153, 154, 155, 156; 623/1.13, 623/1.3, 23.64, 23.65, 1.31
 See application file for complete search history.

(56) References Cited

U.S. PATENT DOCUMENTS

| | | | |
|---|---|---|---|
| 4,809,676 A | | 3/1989 | Freeman |
| 5,116,494 A | | 5/1992 | Chick et al. |
| 5,123,917 A | | 6/1992 | Lee |
| 5,141,516 A | | 8/1992 | Detweiler |
| 5,261,898 A | | 11/1993 | Polin et al. |
| 5,509,888 A | | 4/1996 | Miller |
| 5,549,122 A | | 8/1996 | Detweilwer |
| 5,591,197 A | | 1/1997 | Orth et al. |
| 5,755,778 A | * | 5/1998 | Kleshinski .................. 623/1.13 |
| 5,788,979 A | * | 8/1998 | Alt .......................... A61F 2/062 424/400 |
| 5,843,164 A | | 12/1998 | Frantzen et al. |
| 5,989,276 A | * | 11/1999 | Houser et al. ................ 606/170 |
| 6,091,992 A | | 7/2000 | Bourgeois et al. |
| 6,124,523 A | | 9/2000 | Banas et al. |
| 6,193,734 B1 | | 2/2001 | Boldue et al. |
| 6,395,026 B1 | | 5/2002 | Aboul-Hosn et al. |
| 6,494,908 B1 | | 12/2002 | Huxel et al. |
| 6,602,281 B1 | | 8/2003 | Klein |
| 6,616,675 B1 | * | 9/2003 | Evard et al. .................. 606/155 |
| 6,675,809 B2 | | 1/2004 | Stack et al. |
| 6,767,359 B2 | * | 7/2004 | Weadock .................. A61F 2/07 623/1.14 |
| 6,926,724 B1 | | 8/2005 | Chu |
| 7,037,343 B2 | | 5/2006 | Imran |
| 7,141,071 B2 | | 11/2006 | Imran |
| 7,357,818 B2 | | 4/2008 | Deal |
| 2001/0020189 A1 | | 9/2001 | Taylor |
| 2001/0047180 A1 | * | 11/2001 | Grudem et al. .............. 606/153 |
| 2002/0052572 A1 | * | 5/2002 | Franco et al. ..................... 604/8 |
| 2002/0055770 A1 | * | 5/2002 | Doran et al. ................. 623/1.15 |
| 2002/0087176 A1 | * | 7/2002 | Greenhalgh .................. 606/155 |
| 2002/0151913 A1 | * | 10/2002 | Berg et al. .................... 606/153 |
| 2003/0097172 A1 | * | 5/2003 | Shalev et al. ................. 623/1.31 |
| 2003/0120292 A1 | | 6/2003 | Park et al. |
| 2003/0144708 A1 | | 7/2003 | Starkebaum |
| 2003/0229364 A1 | * | 12/2003 | Seiba ............................ 606/153 |
| 2004/0034320 A1 | | 2/2004 | Burnett |
| 2004/0039452 A1 | | 2/2004 | Bessler |
| 2004/0107004 A1 | | 6/2004 | Levine et al. |
| 2004/0167605 A1 | * | 8/2004 | Elliott .......................... 623/1.13 |
| 2005/0149173 A1 | | 7/2005 | Hunter et al. |
| 2005/0163954 A1 | * | 7/2005 | Shaw ............................ 428/36.1 |
| 2005/0182481 A1 | * | 8/2005 | Schlick et al. ............... 623/1.15 |
| 2005/0228409 A1 | * | 10/2005 | Coppi ........................... 606/153 |
| 2005/0261761 A1 | | 11/2005 | Chu |
| 2005/0273121 A1 | * | 12/2005 | Sato et al. .................... 606/153 |
| 2006/0030920 A1 | * | 2/2006 | Ben-Muvhar .................. 623/1.3 |
| 2006/0129237 A1 | | 6/2006 | Imran |
| 2006/0149349 A1 | * | 7/2006 | Garbe ........................... 623/1.11 |
| 2006/0200178 A1 | * | 9/2006 | Hamel et al. ................. 606/153 |
| 2006/0200199 A1 | | 9/2006 | Bonutti et al. |
| 2006/0229711 A1 | * | 10/2006 | Yan et al. .................... 623/1.38 |
| 2007/0093910 A1 | | 4/2007 | Imran |
| 2007/0207186 A1 | | 9/2007 | Scanlon et al. |
| 2008/0039878 A1 | * | 2/2008 | Williams et al. ............. 606/153 |
| 2008/0051875 A1 | | 2/2008 | Cottone et al. |
| 2008/0114466 A1 | * | 5/2008 | Shelton ......................... 623/23.7 |
| 2008/0255650 A1 | * | 10/2008 | Kelley ........................... 623/1.2 |

FOREIGN PATENT DOCUMENTS

| | | |
|---|---|---|
| JP | 2006523515 | 10/2006 |
| WO | WO 2004/093966 A1 | 11/2004 |

OTHER PUBLICATIONS

First Examination Report dated Aug. 29, 2013 in Australian Application No. 2009276716.
First Office Action dated Mar. 1, 2013 in Chinese Application No. 200980129597.1.
First Office Action dated Jul. 23, 2013 in Japanese Application No. 2011-521252.
Second Office Action dated Dec. 16, 2013 in Chinese Application No. 200980129597.1 in Chinese.
Second Office Action dated Dec. 16, 2013 in Chinese Application No. 200980129597.1 in English.
Office Action dated Jul. 21, 2015 in Japanese Application No. 2014-521252.

* cited by examiner

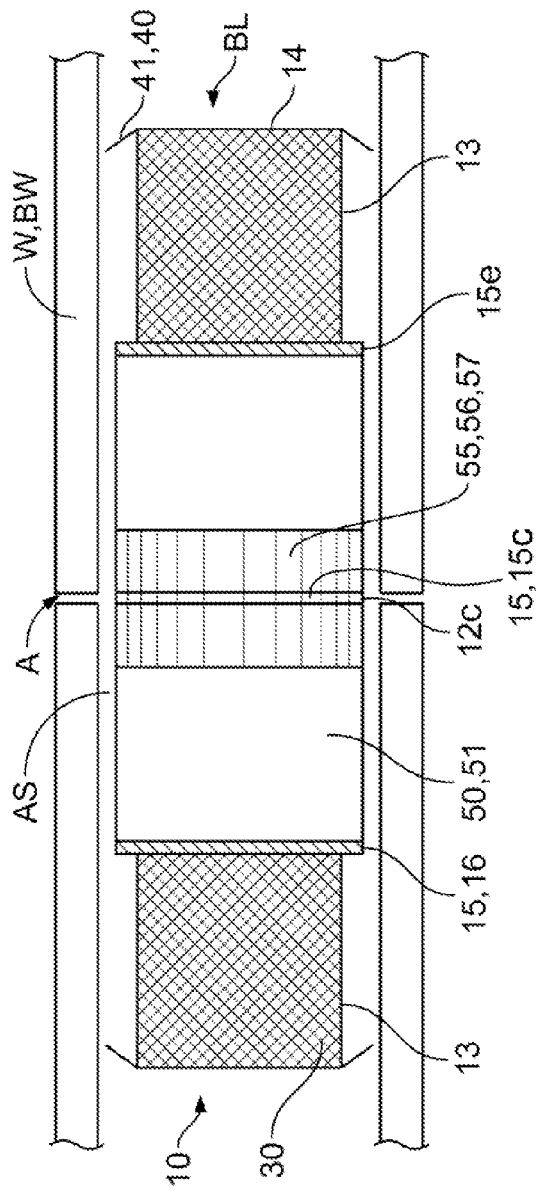
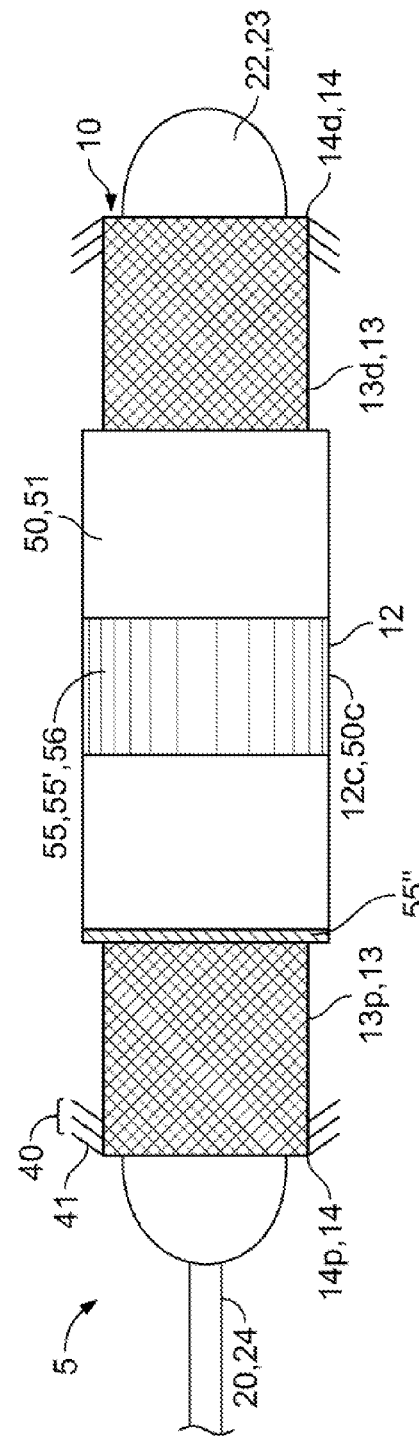

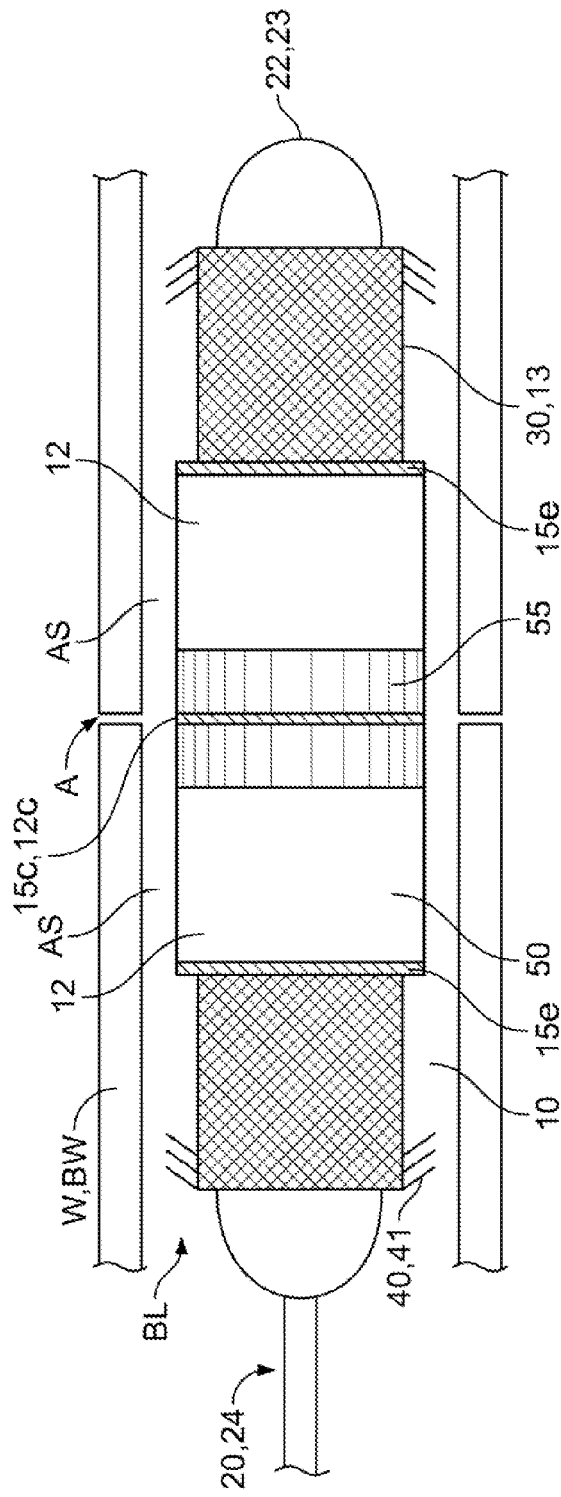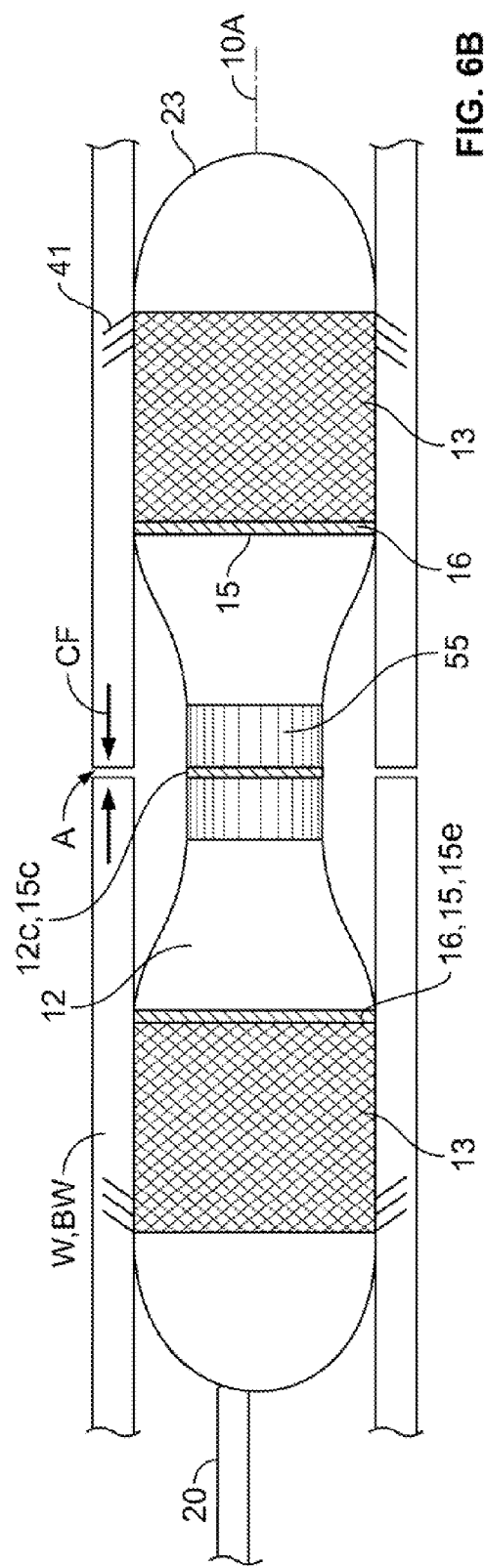

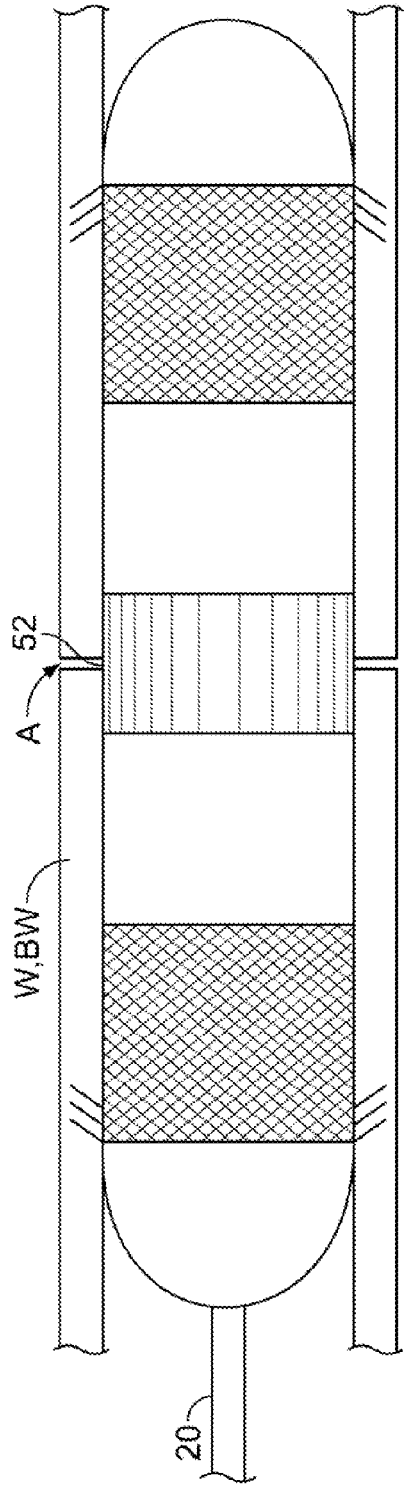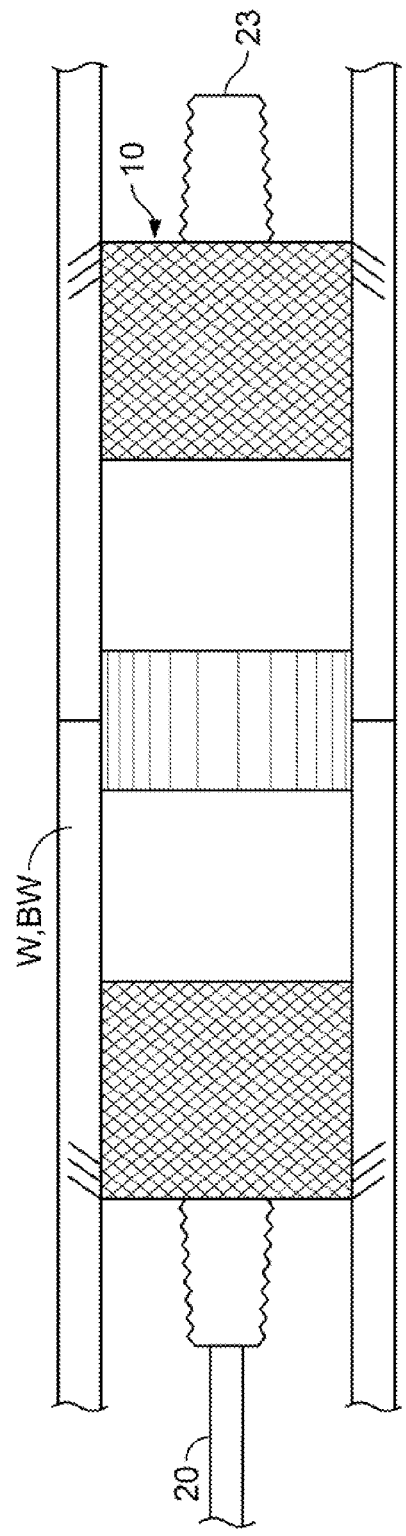

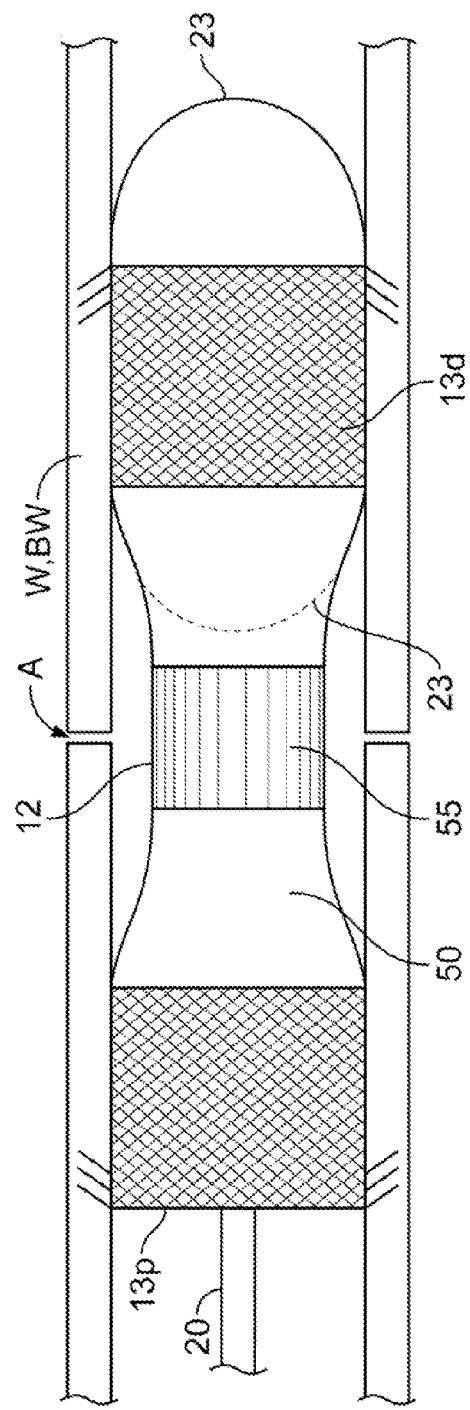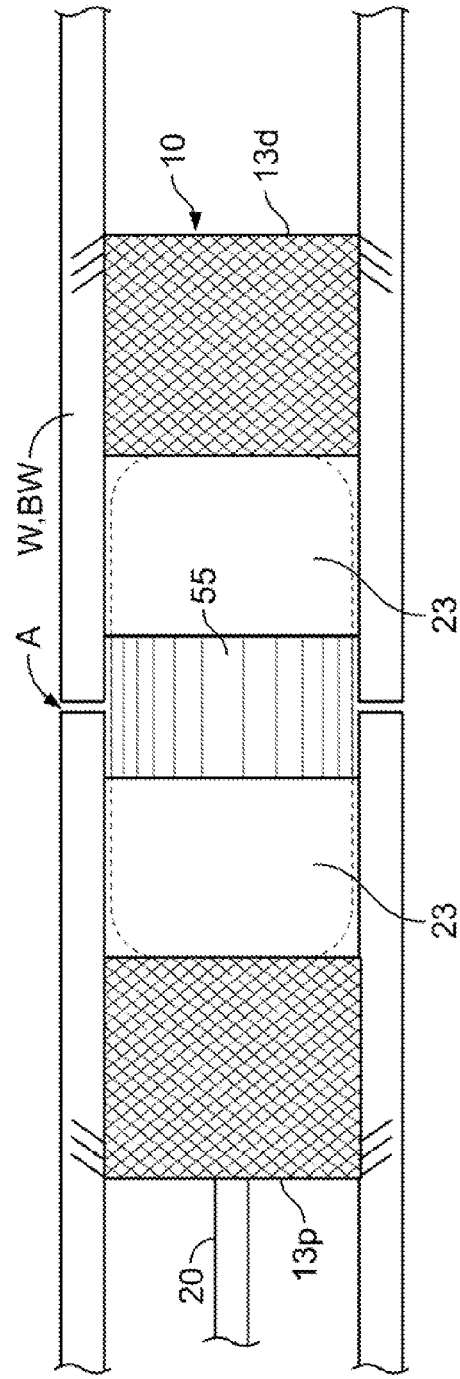
FIG. 7B
FIG. 7C

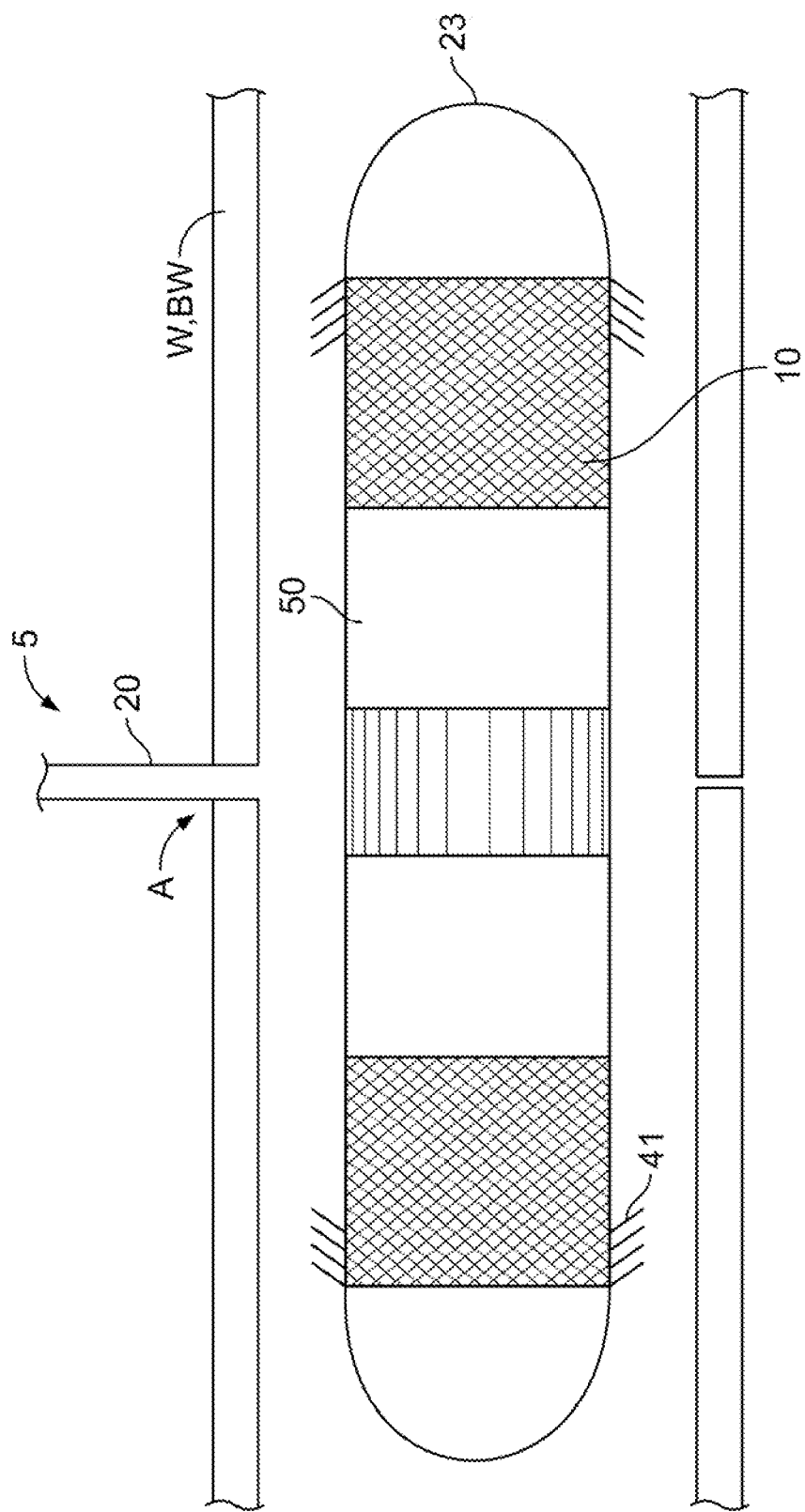

SYSTEM AND METHOD FOR SCAFFOLDING ANASTOMOSES

BACKGROUND OF THE INVENTION

Field of the Invention

Embodiments of invention relate to system and methods for facilitating healing of anastomoses. More specifically, embodiments of the invention relate to systems and methods for facilitating healing of intestinal anastomoses.

There is an ever increasing number of gastrointestinal procedures performed each year. Colon resections alone account for over 600,000 procedures per year in the United States. Colon resection and a number of other of these procedures involve the resection and anastomosis or surgical joining of sections of the intestine, esophagus and other gastrointestinal organs and tissue. However, despite advances in surgical techniques, failed or otherwise poor anastomotic healing is a major challenge in gastrointestinal surgery. Such failed/poor healing results in leakage, infection, stricture and obstruction. Colonic and esophageal resections are associated with some of the highest anastomotic complication rates, due to leakage and stricture formation. For example, the complication rate for colon resection is as high as 50% with mortality rate for patients with anastomotic leaks in the range of 10-15%. The gastric pull-up procedure, a standard intervention after radical esophagectomy, is likewise associated with high morbidity and mortality due to leaks and stricture).

The failure of an anastomosis in the gastrointestinal tract may be caused by several factors. The major problems include the following. Infection at the anastomotic site that interferes with healing and can lead to anastomotic leaks and peritoneal infection. Axial (lateral) and/or radial other tension on the anastomosis (referred to as anastomotic tension) sufficient to pull the two laterals of the anastomosis apart or otherwise interfere with normal healing. Tissue ischemia due to a reduced blood supply at the anastomosis, which can be caused by anastomotic tension and/or excessive suture/staple compression at the anastomosis. Poor tissue apposition caused by an improper alignment of the wound edges in the anastomosis. Finally, the formation of strictures due to narrowing of the intestinal lumen following an anastomosis which leads to intestinal obstruction. Thus, there exists a need for systems and methods to improve anastomotic healing by addressing one or more of these factors.

BRIEF SUMMARY OF THE INVENTION

Embodiments of the invention provide apparatus, systems and methods for using a prosthetic scaffold or other prosthesis to facilitate and/or promote the healing of surgical anastomoses in the intestines, esophagus and other body lumens. Many embodiments provide an expandable prosthetic tissue scaffold that can be positioned at an anastomotic site after a surgical procedure to facilitate healing of the anastomosis through a variety of means. First, the scaffold can include anchors or retention elements at the lateral portions of the scaffold which allow the scaffold to be retained in place at the desired lumen without directly attaching to the anastomosis. This allows the opposing like tissue layers of the anastomosis to be directly joined and thus, readily re-vascularize and heal. The scaffold can also be configured to shorten in length upon expansion so as to put the anastomosis in compression. This minimizes the amount of tensile forces acting on the anastomosis (e.g. due to peristaltic waves), and in turn, reduces the risk of anastomotic tearing and tissue ischemia caused from the anastomotic site being in tension. The scaffold can also include a barrier layer that engages with the lumen wall at the anastomotic site to prevent leakage out of the anastomoses of intestinal contents such as stool and other intestinal fluids. This reduces the risk of infection and inflammation at the anastomotic site.

Embodiments of the prosthetic scaffold are particularly useful for facilitating healing of surgical anastomoses in the large and small intestines and the esophagus. They are also applicable in a variety of other luminal sites in the body including, without limitation, the heart (e.g. a coronary arteries, AV fistula), the liver (e.g. the hepatic duct, the bilary tree etc.), the pancreas (e.g. the pancreatic duct), the gall bladder (the cystic duct), the brain (e.g. a cerebral artery); the genital-urinary system (e.g., ureter, urethra, fallopian tubes, vas deferens) and various sites in the vasculature, e.g., the aorta, the carotid artery, the femoral or other peripheral artery or vein and like site. The size, shape and properties of the scaffold can be adapted for the particular site. For example, in arterial applications, the shape and taper of the scaffold can be matched to that of the artery (e.g., that of the ascending aorta). Also the scaffold can have a non-thrombogenic coating such as heparin.

In addition to placement at a surgically created anastomosis, various embodiments of the scaffold may also be positioned in a body lumen where there is a naturally created tear or dissection (e.g., such as the case with a detached esophagus) to facilitate healing in the same manner as for a surgical anastomosis. In such embodiments, the shape and material properties of the scaffold can be matched to the shape, location and tissue properties of the tear.

In one embodiment, the invention provides a tissue scaffold for placement at an anastomotic site within a body lumen, comprising a radially expandable scaffold structure having two lateral portions and a mid portion, at least one retention element coupled to each lateral portion and a barrier layer. The retention element can comprise a hook that anchors or otherwise engages the intestinal or other lumen wall when the scaffold structure is expanded to retain the scaffold in the body lumen during the period of anastomotic healing. As is explained below, they can also exert a compressive force on the anastomosis. The mid portion of the scaffold can have a greater radial stiffness than the lateral portions such that when the scaffold is expanded (e.g., by a balloon catheter or other expansion mean), the lateral portions expand first and along with the retention elements, engage the lumen wall tissue prior to the mid portion. Since the scaffold will typically shrink in length as the scaffold structure is expanded, this allows the retention elements to exert a compressive force on the anastomosis. Desirably, this force is sufficient to maintain the alignment of opposing tissue layers of the anastomosis.

All or a portion of the scaffold can be fabricated from a bio-absorbable and/or bio degradable material, such that over time after the anastomotic healing has substantially completed, the scaffold is re-absorbed by the body or is otherwise dissolved by hydrolysis from exposure to digestive and other bodily fluids. The rate of re-absorption/degradation can be selected through the choice of materials (e.g., the selected co-polymers and degree of cross linking) and scaffold dimensions and can be titrated for the particular anastomotic site. The barrier layer is configured to engage a tissue wall of the anastomotic site when the scaffold is expanded to provide a fluidic seal at the anastomosis so as to prevent leakage out of the intestine or other body lumen.

The mid portion of the scaffold has sufficient radial stiffness in the expanded state to form and maintain the seal at the anastomosis for extended period of time during which anastomotic healing occurs.

In many embodiments, the scaffold/scaffold structure is configured to be expanded from a non-deployed state to a larger diameter deployed state. This can be achieved through the use of a scaffold stricture that stretches in diameter with the application of force such as that from a balloon catheter or other expansion device. The scaffold structure can also have a varying thickness across the length of the scaffold to produce a desired stiffness profile, for example, so that the lateral portions are stiffer than the mid portions. The scaffold structure can have a variety of patterns. In various embodiments, the scaffold structure can also be configured to yield different shapes for the scaffold in the fully deployed state and also in a partially deployed stated. For example, the scaffold structure can be configured such that the fully deployed scaffold has a dog-bone or other outwardly flared shape, to help stabilize the scaffold at the selected site and prevent migration of the scaffold. It can also be configured to have this shape in the partially deployed state so that the lateral portions of the scaffold engage the lumen wall first before assuming a substantially tubular shape in the final deployed state (this can be achieved through the varying stiffness profile described above). Additionally, the scaffold can be configured to shrink in length in its fully deployed state so as to exert a compressive force on the anastomosis. Desirably, the compressive force is sufficient to maintain the alignment of opposing tissue layers of the anastomosis.

In various embodiments, the barrier layer can comprise a tubular protective member that fits over the mid portion of the scaffold. For gastro-intestinal applications, after the scaffold has been reabsorbed, the protective member can be configured to be passed through the intestines by normal digestive processes. In other applications, the protective member can also be configured to be bio-absorbable at the same or a different rate as that of the scaffold. Preferably, the protective member/barrier layer is constructed from a material that is impermeable to various bodily fluids. For intestinal applications, it is also preferable that the barrier be impermeable to fecal matter and bacteria. The barrier layer can also include one or more coatings or agents to promote healing, reduce inflammation, prevent infection and facilitate collagen deposition at the anastomotic site. The barrier layer may also be covered with a sheet of biological or other material configured to further promote healing at the anastomotic site.

In many embodiments, the scaffold can be delivered using a delivery catheter, which typically can be a balloon delivery catheter known in the art but other delivery means are also contemplated. Both the scaffold and the delivery catheter can also be configured to be delivered using an endoscopic, laproscopic or an open surgical procedure. In various gastro-intestinal applications, the scaffold can be configured to be delivered using an esophageal, rectal approach or an open surgical procedure. The scaffold can also be shaped for doing a variety of anastomotic configurations including without limitation, end-to-end, end-to-side and side-to-side and can have tubular, T-shaped, S-shaped configuration respectively to accommodate these and related anastomoses.

In many embodiments, radio-opaque, echogenic or other medical imaging visible markers will be placed on the scaffold and/or delivery catheter at desired locations. In particular, it may be desirable to provide radio-opaque markers at or near the lateral midpoint on the scaffold and/or at the edges of the barrier layer, this allows the physician to align the midpoint of the scaffold with the anastomosis as well as to assure that there is sufficient length of proactive member/barrier layer on either side of the anastomosis. Markers can also be placed on or at the locations of the retention elements. In embodiments having a bar bell, dog-bone or otherwise outwardly flared shaped scaffold structure, markers can also be placed at transition points on the non-deployed scaffold where the diameter begins to flare out when in the scaffold is in the deployed state.

In an exemplary deployment protocol, the prosthetic scaffold is first positioned at the desired anastomotic site using a delivery catheter such as a balloon catheter. This can be done under direct observation using a viewing scope or through fluoroscopic or other medical imaging means known in the art (e.g., ultrasound). The mid portion of the scaffold is then aligned with anastomosis and the scaffold is expanded using the balloon catheter. The balloon catheter expands the scaffold within the selected body lumen until the scaffold, including the retention elements and the protective member, engages the body lumen. The balloon can continue to be expanded somewhat to press the protective member against the anastomosis and set the retention elements in the lumen wall and so affix the scaffold in place (this can also be facilitated by tugging on the delivery catheter to set the retention element in the same way as a fishing hook). For embodiments having an outwardly flared scaffold in the partially deployed state, the balloon is first expanded to have the lateral sections including the retention element engage the lumen wall and then continued to be expanded until the scaffold mid portion including the protective member engages and seals against the anastomosis. The balloon is then deflated and withdrawn from the interior of the scaffold with the scaffold now in a fully deployed state wherein the retention elements are set and the protective member has formed a seal against the anastomosis. In many embodiments, the amount of expansion can be assessed by inflating the balloon with a radio-opaque dye known in the art. The final diameter of the scaffold can be controlled both through the construction of the scaffold structure and/or the use of inelastic expansion balloon.

Typically, the entire scaffold will be expanded at the same time; however, in some cases, the scaffold can be expanded segmentally and specific embodiments of the scaffold can be configured for such segmental expansion. For example, one lateral portion of the scaffold can be expanded first, then other lateral portion and then the mid portion. Alternatively, the mid portion could be expanded first and then the lateral portions. This can be done using the same or different balloon catheters. For example, a first balloon having a particular inflated diameter could be used for expansion of the lateral portions and second balloon having a smaller diameter could be used for inflation of the mid portion, or the second balloon could have the larger diameter. In still other situations, a first balloon having a first diameter could be used for expansion of one lateral portion of the scaffold and another different sized balloon for the other lateral side and still a third for the mid portion. Such a procedure could be used for end-to-side anastomoses or side to side anastomoses where portions of the scaffold lie in body lumens having different diameters. It is also applicable for body lumens having a varying diameter across the length of the lumen (e.g., where the sigmoid colon joins the rectum) or where one of the lateral portions is placed at the opening of the body lumen (e.g., where the cardia of the stomach joins esophagus). Further details of these and other embodiments and aspects of the invention are described more fully below.

BRIEF DESCRIPTION OF THE DRAWINGS

FIG. 1 is a lateral view showing an embodiment of the prosthetic scaffold of the present invention mounted positioned at an anastomosis.

FIG. 2 is a lateral view showing an embodiment of the prosthetic scaffold of the present invention mounted over a delivery catheter.

FIGS. 6a-6e are lateral views illustrating a method of deployment of the prosthetic scaffold at an anastomotic site using a balloon delivery catheter.

FIGS. 7a-7c are lateral view illustrating a method of segmental deployment of the prosthetic scaffold using segmental expansion of a balloon delivery catheter.

FIGS. 8a-8b are lateral view illustrating a method of deployment of the prosthetic scaffold via access through the anastomosis or other opening in the bowel or lumen wall. FIG. 8a shows the scaffold in a non-deployed state and FIG. 8b shows the scaffold in a deployed state.

FIG. 11a illustrates use in an anastomosis having an aligned intestine and FIG. 11b illustrates use in an anastomosis having offset body lumens.

DETAILED DESCRIPTION OF THE INVENTION

Figure 3:
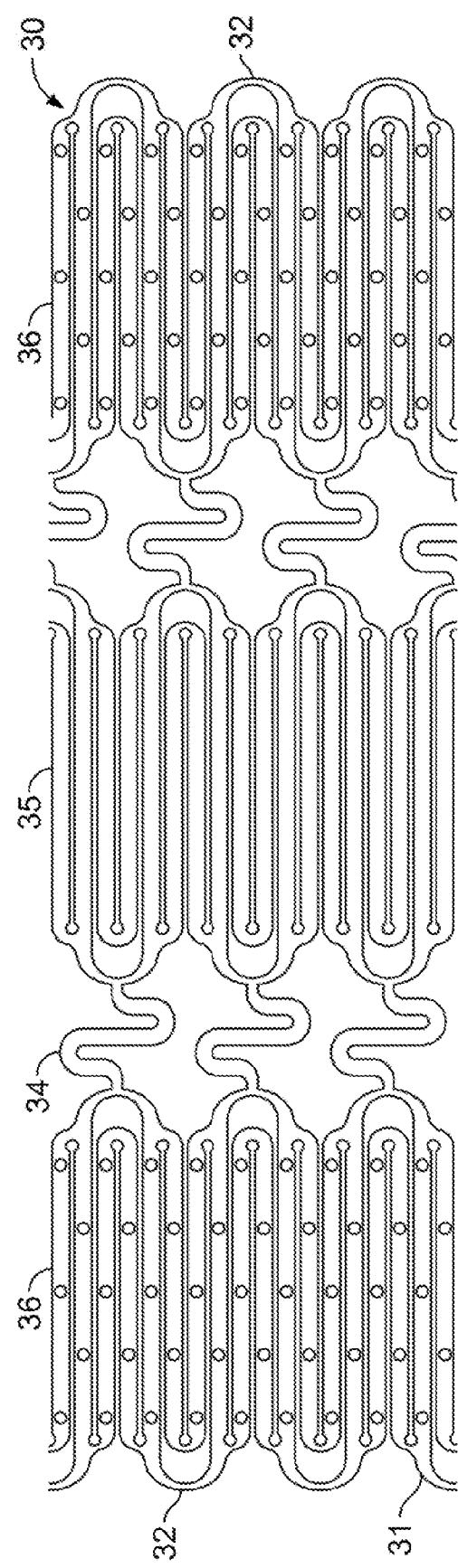
FIG. 3 is a lateral view illustrating an embodiment of a scaffold structure shown in a rolled Out pattern.

Embodiments of the invention provide apparatus, systems and methods for using a prosthetic scaffold or other prostheses to facilitate and/or promote healing of surgical anastomoses in the intestines, esophagus and other body lumens. Many embodiments provide an expandable prosthetic scaffold that can be positioned at an anastomotic site after a surgical procedure to facilitate both closure and healing of the anastomosis. As used herein, the term surgical anastomosis or anastomoses refers to a surgical connection or re-connection between ducts, tubes or vessels in the body. It may be end-to-end, end-to-side, side-to-end, or side-to-side.

For ease of discussion, the term will typically be used in reference to an end-to-end junction, but the other applications are equally applicable to embodiments herein. Also it should be understood that the embodiments of the scaffold described herein have wide application to a number of lumens throughout the body, but for ease of discussion, the following description will be referring to use of the device in the intestines, typically the large intestine, but all other tissue sites described herein are equally applicable.

Referring now to FIGS. 1-5, an embodiment of a system 5 for the delivery and deployment of a tissue prosthetic scaffold to an anastomosis A within the wall, W, of an intestine or other body lumen, BL can include a scaffold 10 and a delivery catheter 20. Scaffold 10 includes a mid section 12, lateral sections 13, including proximal and distal sections 13p and 13d; and ends 14 including proximal and distal ends 14p and 14d. All or a portion of scaffold 10 includes a radially expandable scaffold structure 30, an anchor structure 40, including one or more anchors 41 also known as retention elements 41 and a barrier layer 50. Barrier layer 50 can also include one or more coatings or biological layers 55 including various medicaments or agents 56 discussed herein.

In many embodiments, scaffold 10 is configured to be delivered to the anastomotic site by means of a delivery catheter 20. The delivery catheter can be a balloon delivery catheter 24 having an inflatable balloon 23, but other delivery means are also contemplated. The scaffold can be attached to the delivery catheter by several means including, adhesive bonding (using a releasable adhesive), crimping or through the use of a restraining sheath or covering. Both the scaffold and the delivery catheter can also be configured to be delivered using an endoscopic, laparoscopic or an open surgical procedure. The length and inflated diameter of the delivery catheter can be sized for the particular procedure, approach and selected anastomotic site. For endoscopic procedures, the length of the delivery catheter can be in the range of 100 to 150 mm, with specific embodiments of 110, 120, 130 and 140 mm.

Scaffold 10 can also be sized and shaped for the particular body lumen and anastomotic site, AS. In many embodiments, scaffold 10, has a generally cylindrical shape which can be used in various end-to-end anastomoses. It may also have an outwardly flared shape such as a dog bone or bar bell shape, particularly in a semi-deployed state discussed herein. Other shapes are also contemplated including U, S and T shapes as are discussed in further detail herein. The deployed length 10L' and deployed/expanded diameter 10D' of the scaffold can be sized for the particular lumen and anastomotic site AS. For applications in the small in the small intestine the expanded diameter 10d of the scaffold can be in the range of 2 to 4 cms, with a specific embodiments of 2.5 and 3 cms, while for large intestine applications the expanded diameter can be in the range of 6 to 9 cms with specific embodiments of 7, 7.5, and 8 cms. Other diameters for other body lumens are also contemplated. The length 10L of the scaffold can from range from 2 to 30 cms 30 cms with specific embodiments of 2.5 5, 7.5, 10, 15, 20 and 25 cms. The final expanded diameter can be controlled using balloon 23 or other expansion device as a sizing device.

Typically, scaffold 10 is configured to be expanded from a non-deployed state to a larger diameter deployed state to facilitate delivery using minimally invasive methods. This can be achieved through the use of a scaffold structure that stretches in diameter with the application of force such as that from a balloon catheter or other expansion device. Accordingly, in many embodiments, scaffold 10 comprises an expandable structure that typically will be expandable by an expansion device 22 such as a balloon 23 that is part of a balloon deliver catheter 24. Other expansion devices known in the minimally invasive surgical arts are also contemplated. Alternatively, scaffold 10 can also be configured to be self expandable for example, using shape memory materials know in the art in which the scaffold is held in a constrained state and then released. For expandable embodiments, scaffold 10 has a non deployed state (FIG. 6a) and a fully deployed state (FIG. 6c). It may also have a partially deployed state, for example, that shown in FIG. 6b which has a dog bone, bar bell or other outwardly flared shape with respect to the lateral axis 10A of the scaffold. Typically, scaffold 10 will be carried on the delivery catheter 20 in the non-deployed state and put into the deployed state once positioned at the desired anastomotic site. The scaffold can also be put in the partially deployed state to facilitate engagement of retention elements 41 with the bowel wall BW or other lumen wall W. Typically, this will be done by expanding the scaffold lateral sections 13 to engage the bowel wall first (along with retention elements 41) and then fully expand the scaffold so that the mid portion engages the bowel wall. For embodiments where the scaffold laterally contracts in the deployed state (discussed herein), this allows retention elements 41 to exert a compression force on the bowel wall and in turn, the anastomosis.

Referring now to FIG. 3, a discussion will be presented of the structure of scaffold 10. In various embodiments, scaffold structure 30 can have a variety of patterns including, criss-cross, spiral, serpentine or a combination thereof. It will be appreciated that a wide variety of other patterns known in the art are equally applicable for use in scaffold structure 30. In an exemplary embodiment of scaffold 10 shown in FIG. 3 in a rolled out pattern, scaffold structure 30 comprises a plurality of radially expansible serpentine cells 32 formed from a strip 31. Cells 32 are joined by smaller expansible members 34. In this and related embodiments, scaffold 30 is divided into a mid section 35 and two lateral sections 36 which correspond to lateral sections 13 and mid section 12. Typically, the strip thickness of mid sections 35 is greater than the thickness of lateral sections 36. This provides mid section 12, with a greater amount of radial stiffness versus lateral sections 13, 36. Such configurations also allow lateral sections 13, 36 to be expanded first (from the outward radial force of a balloon catheter or other expansion device) and so have sections 12 including retention elements 41 engage the bowel wall BW prior to engagement by mid section 13. Since in many embodiments, the scaffold structure shrinks laterally as it expands, this allows the scaffold to exert a compressive force on the anastomosis. In this way, the scaffold functions as a mechanical clamp for the anastomosis. The radial stiffness of all or a portion of the scaffold including mid section 35, 12 can also be configured such that the scaffold mechanically supports and buttresses anastomotic site AS including anastomosis A. Desirably, the radial stiffness of at least mid section 12/35 is sufficient to maintain the fluidic seal at the anastomosis and the integrity of the anastomotic joint during movement of the intestine from digestion (e.g., peristaltic waves) or other physiologic functions as well as patient movement. In this way, the scaffold serves as a mechanical support for the anastomosis and anastomotic site to facilitate healing of the anastomosis and reduce the risk of various post operative complications including stricture formation at the anastomosis, infection and inflammation (e.g., from anastomotic leakage) and anastomotic detachment. Other means for increasing the radial stiffness of mid sections 12, 35, relative to lateral sections 13,36 can include the use of carbon nanotubes or other stiffening additives in those sections as well as increased cross linking of the mid sections, for example through the use of e-beam or other irradiation techniques known in the art.

Figure 4A:
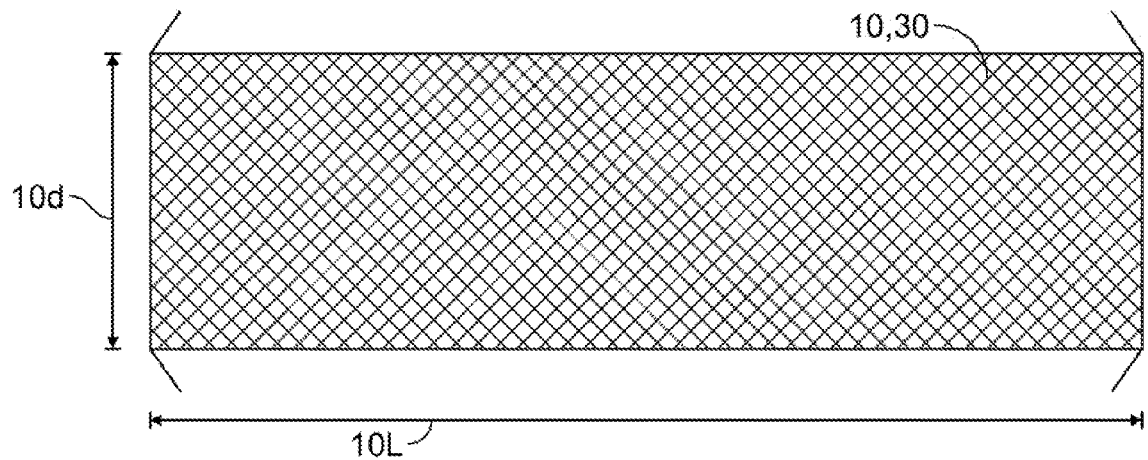
FIGS. 4a and 4b are lateral views showing an embodiment of the prosthetic scaffold in a non-deployed (FIG. 3a) and a deployed state (FIG. 3b) which illustrate shortening of the scaffold in the deployed state.
Figure 4B:
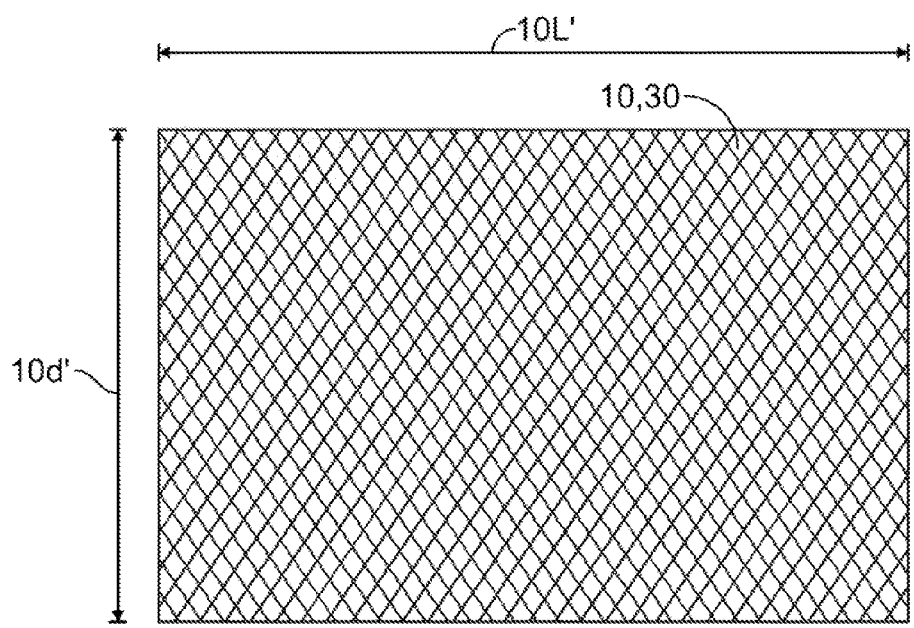
Figure 5A:
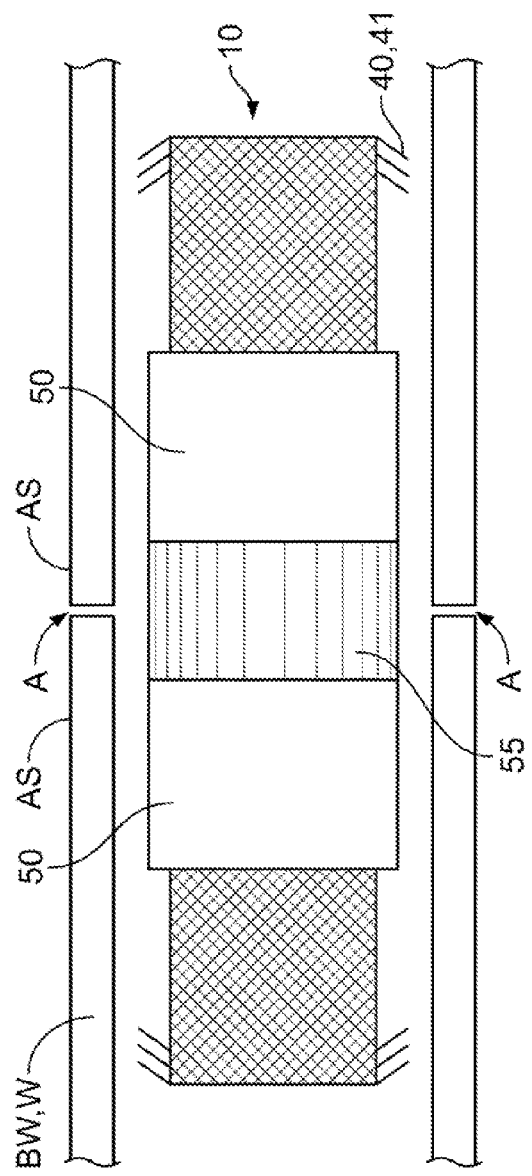
FIGS. 5a and 5b are lateral views showing an embodiment of the prosthetic scaffold in a non-deployed (FIG. 5a) and a deployed state (FIG. 5b) when positioned at an anastomosis which illustrate compressive forces exerted on the luminal wall of the anastomotic site.
Figure 5B:
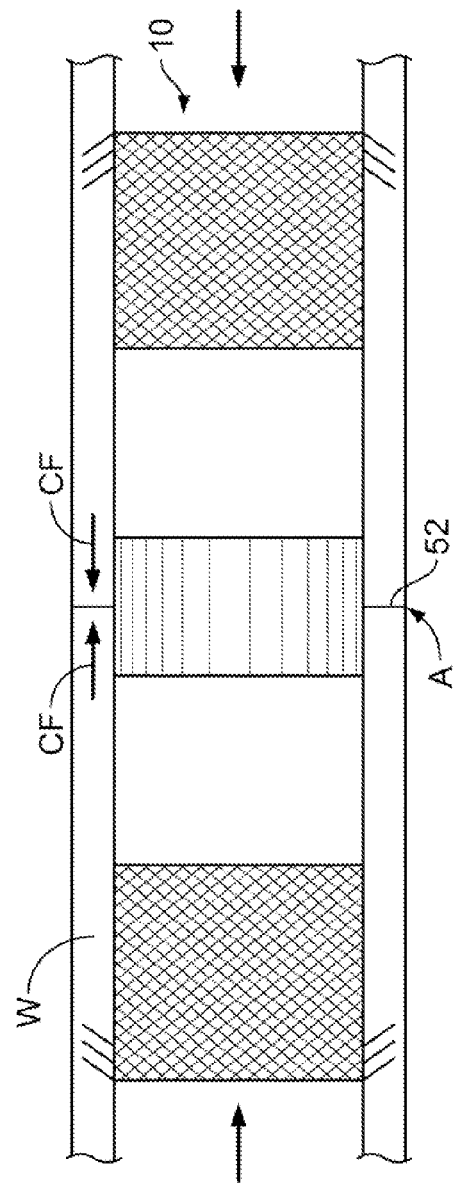

Referring now to FIGS. 4-5, in many embodiments, scaffold 10 is configured to shrink in length as it expands in diameter as is shown in the embodiment of FIGS. 4a and 4b. In this embodiment, the scaffold shrinks in length from L' in to L", while expanding in diameter from D' to D". This can be achieved through the particular configuration of expansible cells 32 which are themselves configured to expand in diameter and shrink in length. The amount of contraction in length can be in the range from 5 to 50%, with specific embodiments of 10, 20, 30, and 40%. While the amount of expansion in diameter can be in the range from 10 to 200%, with even greater amounts of diametric expansion contemplated. Referring now to FIGS. 5a and 5b, through the use of retention elements 41, the effect of this shrinkage is to exert a compressive force CF on the lumen wall W of selected anastomotic site AS. Force CF acts to close the anastomosis and also serves to maintain the alignment of opposing tissue layers in the bowel wall. Force CF also acts to keep the anastomosis in a closed state and/or prevent tearing or other failures by acting against any tensile forces the anastomosis is subjected to from various physiological functions (e.g., peristaltic waves and other digestion movement) as well as patient movement. Force CF thus acts as a stressing force which increases the strength of the healing anastomosis. Keeping the anastomosis in a closed state facilitates healing by preventing leakage of materials form the lumen causing infection or inflammation. In various embodiments, the amount of compressive force can be in the range of 0.1 to 2 lbs, with specific embodiments of 0.5, 0.75, 1.0 and 1.5 lbs. Greater and lesser amounts of force area also contemplated and the force can be titrated to the specific anastomotic site AS. The compressive force from such embodiments is not only beneficial in keeping the anastomosis closed and minimizing tears, but also minimizing and/or offsetting the amount of tensile force to which the anastomosis is subjected. Tensile forces are potentially detrimental to anastomotic healing because in addition to tearing, they can cause ischemia to growing tissue at the anastomotic site (or otherwise reduce the amount of adequate perfusion) by shrinking or squeezing blood vessels (including capillaries) supplying blood and nutrients to the site. In this way, embodiments of a laterally contracting scaffold function to enhance anastomotic healing by minimizing ischemia to tissue at the anastomotic site or otherwise helping to maintain adequate perfusion to the site. As is discussed in further detail herein, such embodiments also serve to promote healing by keep opposing tissue like layers in apposition.

In many embodiments, all or a portion of scaffold 10 including scaffold structure 30 can be fabricated from a bio-resorbable or biodegradable polymer (for ease of discussion referred to as bio-resorbable). Suitable bio-resorbable materials include polymers of lactide, glycolide, lactic acid, glycolic acid, para-dioxanone, caprolactone, and trimethylene carbonate, caprolactone, blends thereof and copolymers thereof. In a preferred embodiment, the material comprises a polylactic-co-glycolic acid (PGLA) such as a high molecular weight polylactic-co-glycolic acid. In various embodiments, the bio-resorbable polymer may be reinforced with nanotubes or carbon fibers. It may also be combined with radio-opaque materials known in the art to render all or selected portions of the scaffold radio-opaque, such as markers 15 discussed herein. In alternative embodiments, the scaffold can be constructed from shape memory super elastic materials such as NITINOL. Such embodiments can be configured to be permanently left in place, to be surgically removed or to be passed through intestinal tract.

Upon in vivo exposure to fluids in the intestine or other body lumen, the bio-resorbable material is configured to be either completely absorbed or cause the scaffold to soften and collapse into a flexible mass that can readily pass out of the intestine or other body lumen. The rate at which the scaffold structure degrades/absorbs can be controlled by selection of the material, the dimensions (e.g., thickness) or both. In particular embodiments, the molecular weight of the material comprising the scaffold structure can be used to control the rate of degradation, with lower molecular weight materials being selected for faster degradation rates and vice versa. Through the choice of one or both of scaffold materials and dimensions, the degradation rate can be titrated so the scaffold lasts for a selectable period depending upon the anastomotic site, body lumen, etc. Slower degradation rates with longer corresponding scaffold residency periods can be selected for example, for large diameter and/or complex anastomoses which otherwise take longer to heal. Faster rates can be selected for smaller and/or faster healing anastomoses.

The retention structures 40 and retention elements 41 are arranged and configured to retain scaffold 10 at the selected anastomotic site in the intestine or other body lumen during the period of anastomotic healing. Such healing periods can be in the range of 1 to 8 weeks with specific embodiments of 2, 4 and 6 weeks. Longer periods are also contemplated including periods of 3, 6 and 12 months. Such longer periods can be achieved through the use of cross-linked, high molecular weight and/or thicker material for the scaffold structure. For intestinal applications, they are configured to provide sufficient retaining force to prevent the scaffold from migrating due to movement of the intestine from peristaltic contractions and other physiologic functions as well from patient movement. They also serve to exert a compressive force on the bowel or other lumen wall for embodiments having scaffold structure that laterally shrinks upon expansion. Retention structure 40 comprises one or more retention elements 41. Typically, the retention structure will comprise a group of two or more retention elements. Groups of three, four, five, and six or more are also contemplated. Retention elements 41 can comprise a hook, pin, barb, helical coil or other retaining means. The length can be selected for the particular body lumen, but can be in the range of 1-5 mm, with specific embodiments of 2, 3 and 4 mms. Their length, diameter, shape and other dimension can be selected for the particular anastomotic site. They may also be straight or angled in a particular direction. Typically, they will be angled toward the midpoint of the scaffold. They can be integral or adhesively attached to the scaffold structure. They can also be reinforced with carbon nano-tubes and may include radio-opaque or other material to function as markers 15 described herein. They may also have a selected amount of spring force which can be achieved by re-enforcement with carbon nano-tubes or other re-enforcing material.

In various embodiments, barrier layer 50 can comprise a protective member or tubular sleeve 51 that fits over scaffold structure 30 and is attached by adhesive bonding or other attachment method known in the art (e.g., ultrasonic welding). Barrier layer 50 can be coated onto scaffold structure 30 using various coating methods known in the art. Typically, protective member 51 will have a cylindrical shape that approximately matches that of scaffold structure 30. But it may also have other tubular shapes as well which are selected to match the shape of the scaffold structure. Such shapes can include curved, U-shaped, S-Shaped, T-shaped and like shapes. As well be discussed below, the barrier layer can also be flexible enough to conform to the shape of the scaffold structure. The barrier layer can cover all or a portion of the scaffold structure, but typically will only cover the mid-portion. Typically, the barrier layer will be centerly positioned at the mid portion 12 of scaffold 10 and desirably and has sufficient length as to extend laterally on either side of the scaffold center 12c so as to form and maintain a fluidic seal of the selected anastomosis as is described below. In other embodiments, the barrier layer can be positioned off-center on the scaffold.

Barrier layer 50 can be configured to perform several different functions. Primarily, it serves as a barrier to prevent the leakage of the contents of the intestine or body lumen out through the healing anastomosis. For intestinal applications, this reduces the risk of infection and inflammation at anastomotic site, AS. Accordingly, in many embodiments barrier layer 50 is configured to engage a tissue wall of the anastomotic site AS when scaffold 10 is expanded to provide a fluidic seal 52 at the anastomosis sufficient to prevent leakage of the contents of the intestines or other body lumen out of the anastomosis into surrounding tissue. Barrier layer 50 also desirably provides a biocompatible surface at the anastomosis and surrounding tissue to facilitate cell growth and healing within and around the anastomosis. The layer is also desirably sufficiently flexible to bend and flex with the movement of the scaffold and still maintain a fluidic seal. Accordingly, in various embodiments, barrier layer 50 can comprise a fluid impermeable flexible biocompatible material known in the art. Suitable materials for barrier 50 include expanded PTFE or other fluoropolymer, silicones, urethanes and copolymers thereof. For various intestinal and vascular applications, barrier layer 50 desirably has sufficient burst/leak strength to maintain a fluidic seal in the face of various physiologic pressures within the selected body lumen (e.g., arterial pressure or that from peristaltic waves). Suitable high strength materials include PTFE or other fluoropolymer, polyethylene, and polyethylene terephthalate (PET) and NYLON. For intestinal and other GI applications barrier layer 50 can also be configured to be absorbed itself or for non-absorbable embodiments, to easily pass through the digestive tract once scaffold 10 has been substantially absorbed. For absorbable/bio-degradable embodiments, barrier 50 can be fabricated from one or more bio-absorbable and/or bio degradable materials described herein including for example, PGLA. The degradation/absorption rate of barrier layer 50 can be configured to be sufficiently slower than the scaffold structure such that the barrier layer outlasts the scaffold structure. This can be achieved through the selection of materials and dimensions of the barrier layer, e.g. using higher molecular weight and/or cross linked bio-absorbable/biodegradable polymers.

In many embodiments, barrier layer 50 can also include a coating or biological layer 55 containing various medicaments, therapeutic or other biological agents 56 to promote healing, reduce inflammation and facilitate collagen and cellular deposition at anastomotic site AS. Biological layer 55 can cover all or a portion of barrier layer 50 and is desirably centrally aligned with respect to midpoint 12c so as to be able to deliver agent 56 directly to anastomosis A and the surrounding anastomotic site AS. Biological layers 55 can also include at least a first and a second biological layer 55' and 55", for example a first biological layer 55' centrally positioned over the midpoint of the scaffold structure and/or barrier layer and a second biological layer 55" positioned near the edge of barrier layer. First and second layers 55' and 55" can also contain different biological agents 56 or contain different concentrations of the same agent, e.g., to produce a two phase delivery of a particular agent.

In various embodiments, agents 56 can include without limitation: VEGF or other growth factor, factors to facilitate wound healing and collagen deposition, antibiotics or other anti-bacterial agent to reduce the risk of infection, dexamethasone, or other steroid or anti-inflammatory agent to reduce inflammation and heparin or other anti coagulant or non-thrombogenic agent (for vascular applications). In preferred embodiments, agents 56 include a combination of VEGF and dexamethasone to promote growth and reduce inflammation. Agents 56 can also be coupled with an eluting or other carrier compound 57 known in the art to control the release of agent 56 into the surrounding anastomotic site. The eluting agents can be configured to yield both short and long term release rates of the desired agent(s) 56, e.g. a short-term fast release followed by a longer-term slower release rate. Other differential release rates are also contemplated (e.g., steady state and non-steady state). Suitable carrier compounds 57 can include various silicones, polyurethanes and other biocompatible permeable polymers known in the art. In addition to providing for the release of various biological agents, biological layer 55 can also be configured to serve as a substrate for the growth of new tissue at the anastomosis before being subsequently re-absorbed. In such embodiments, layer 55 can comprise PGLG, or other bio-absorbable material described herein or known in the art In many embodiments, radio-opaque, echogenic or other medical imaging visible markers 15 can be placed on scaffold 10 at one or more selected locations. In particular, it may be desirable to provide markers 15 at or near the lateral mid-point 12c on the scaffold 10 and/or at the edges of barrier layer 50, this allows the physician to align the center of the scaffold with the anastomosis A as well as to assure that there is sufficient length of barrier layer on either side of the anastomosis. In a particular embodiment, markers 15 can include a marker 15c placed at scaffold center 12c and markers 15c placed at the edges of barrier layer 50. Markers 15 can also be placed on or at the locations of retention elements 41. In embodiments having a bar bell, dog-bone or otherwise outwardly flared shaped scaffold structure, markers 15 can also be placed at transition points 16 on the non-deployed scaffold where the diameter begins to flare out when in the scaffold is in the deployed state. Markers 15 can also be arranged and placed on scaffold structure 30 to serve as indicators of the amounts of degradation of the scaffold. This can be achieved by configuring certain makers to be of fixed length, width, area or other dimension, and then measuring the decrease in that dimension. Such degradation indicators can be used by the physician to assess one or more of the following: i) the amount and rate of degradation of the scaffold; ii) the amount and rate of healing of the anastomosis, iii) any tearing or failure of the anastomosis; iv) if the scaffold needs to be replaced; and v) if surgical intervention is required.

Figure 6E:
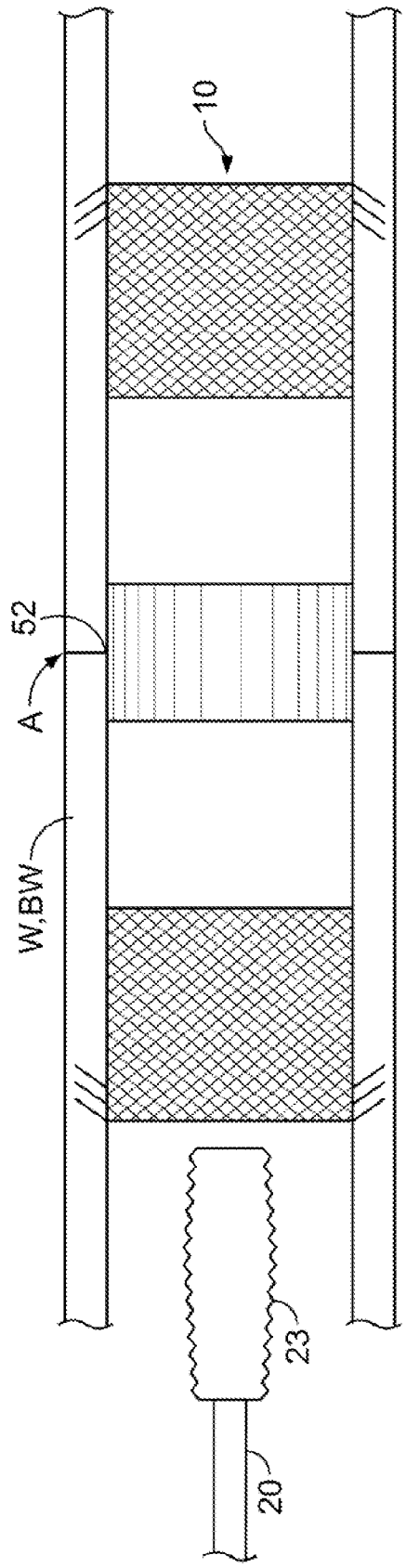

Referring to FIGS. 6a-6e, an exemplary deployment protocol for scaffold 10 will now be presented. This protocol can be adapted for use in an endoscopic, laparoscopic, or an open surgical procedure. First, the prosthetic scaffold is positioned at the desired anastomotic site using a delivery catheter such as a balloon catheter, as is shown in FIG. 6a. For endoscopic procedures, this can be done using either an oral or rectal approach, where the delivery catheter is advanced directly through the GI tract or a through a lumen of the endoscope or other guiding catheter, while for a laparoscopic procedure, the delivery catheter can be advanced through a trocar or other port device. Also, positioning of the delivery catheter can be done under direct observation using a viewing scope or other viewing means or through fluoroscopic or other medical imaging means known in the art (e.g., ultrasound). The mid-point 12c of the scaffold is then roughly aligned with anastomosis A and the scaffold is expanded using balloon catheter 24. This can be facilitated by the use of a central marker 15c on scaffold 10 or markers 15e on the edges of barrier layer 50. The balloon catheter expands the scaffold within the selected body lumen until scaffold 10 including the retention elements 41 and barrier layer 50, engage the body lumen (as is shown in FIG. 6c). The balloon can continue to be expanded somewhat to press the barrier layer against the anastomosis and set the retention elements in the lumen wall and so affix the scaffold in place. This can also be facilitated by tugging on the delivery catheter to set the retention element in a similar way as a fishing hook. For embodiments having an outwardly flared scaffold in the partially deployed state (see FIG. 6b.), the balloon is first expanded to have the lateral sections 13 including retention elements 40 expand and engage the lumen wall W (as is shown in FIG. 6b) and then continued to be expanded until the scaffold mid portion 12 including barrier layer 50 engages and seals against the anastomosis. This embodiment also illustrates how scaffold 10 exerts a compressive force CF on bowel wall BW or other lumen wall W so as to help close the anastomosis and maintain it in a closed state. This occurs by having retention elements 41 first engage the bowel wall and then as the scaffold is continued to be expanded, it shrinks in length such that the retention elements exert a compressive force CF to pull the two half's of the bowel wall together. As is discussed herein, this compressive force helps to maintain the anastomosis in a closed state by overcoming tensile forces on the anastomosis occurring from pulling or movement of the body lumen as occurs during digestion, respiration or patient movement. As is discussed herein, reduction of the tensile forces on the anastomosis also serves to promote anastomotic healing by maintaining adequate perfusion to the anastomotic site by preventing the vasculature at the site from being compressed due to such tension.

After complete inflation, the balloon is then deflated (as is shown FIG. 6d) and withdrawn from the interior of the scaffold (as is shown FIG. 6e) with the scaffold now in a fully deployed state wherein the retention elements are set and the protective member has formed a seal 52 against the anastomosis. In many embodiments, the amount of expansion of the balloon and thus the scaffold can be assessed by inflating the balloon with a radio-opaque dye known in the art. It can also be assessed by measurement of markers 15 through direct imaging. The final diameter of the scaffold can be controlled both through the construction of the scaffold structure and the use of an inelastic expansion balloon.

Figure 7A:
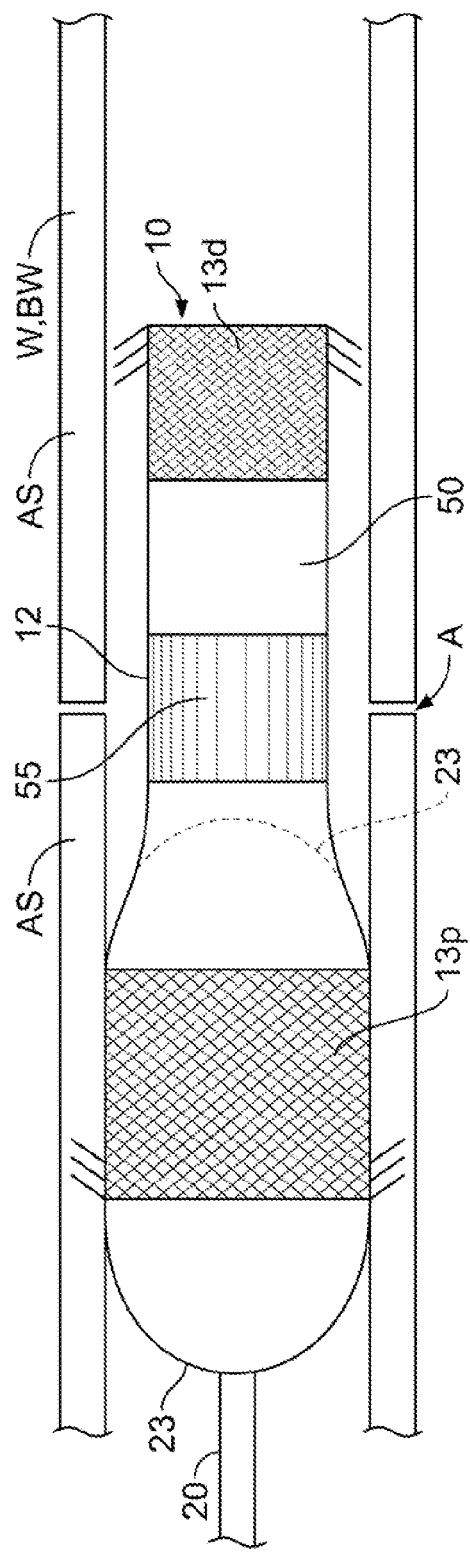

Typically, the entire scaffold will be expanded at the same time; however, in some cases, the scaffold can be expanded segmentally and specific embodiments of the scaffold can be configured for such segmental expansion. Referring now to FIGS. 7a-7c, in one embodiment of a segmental expansion protocol, one lateral portion 13 of the scaffold can be expanded first (e.g., the proximal portion, 13p as is shown in FIG. 7a), then other lateral portion (as is shown in FIG. 7b), and then the mid portion 12 (as is shown in FIG. 7c). Alternatively, the mid portion could be expanded first and then the lateral portions. These and other embodiments of segmental expansion techniques can be done using the same or different balloon catheters. For example, a first balloon having a particular inflated diameter could be used for expansion of the lateral portions 13 and a second balloon having a smaller diameter could be used for inflation of the mid portion 12. Segmental expansion protocols can be used in a number of situations, such as where the selected anastomotic site is in extremely curved or convoluted portion of the intestine or other body lumen. This approach allows the physician to expand and fix one portion of the scaffold first using the retaining elements before doing another section. This reduces the likelihood of the scaffold popping Out of the curved portion if it is inflated all at once. Segmental expansion can also be used for inflating T-shaped or other shaped scaffolds configured for use in a side-to-end anastomosis.

In still other embodiments, a first balloon having a first diameter could be used for expansion of one lateral portion of the scaffold and another different sized balloon for the other lateral side and still a third for the mid portion. Such a procedure could be used for end to side anastomoses or side-to-side anastomoses where portions of the scaffold lie in body lumens having different diameters. It is also applicable for body lumens having a varying diameter across the length of the lumen (e.g., where the sigmoid colon joins the rectum) or where one of the lateral portions is placed at the opening of a body lumen (e.g., where the cardia of the stomach joins esophagus).

Figure 8B:
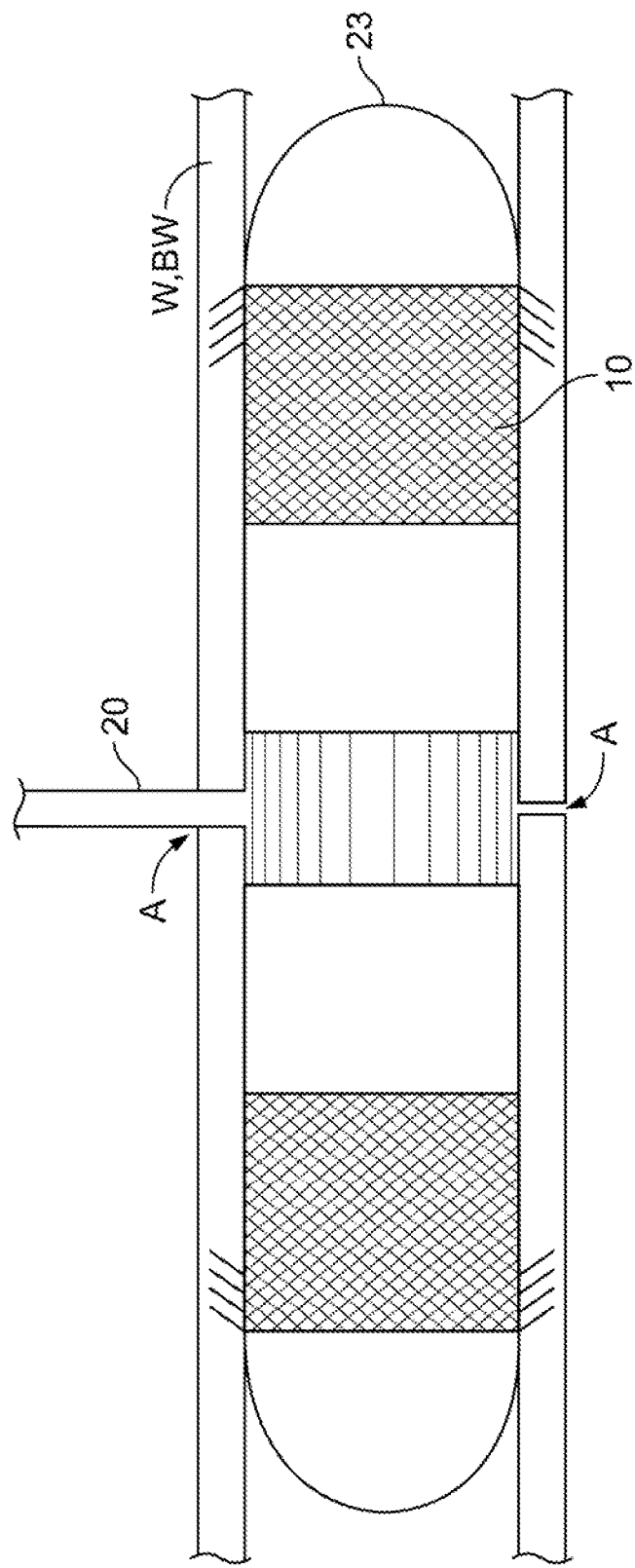

As discussed herein, in various GI applications, scaffold 10 can be configured to be delivered to the anastomotic site either through an oral or rectal approach. In such embodiments the balloon catheter used to expand the scaffold is inflated from the proximal end of the scaffold (via an attached catheter) and also withdrawn from that same end. Referring now to FIGS. 8a-8b, however; in other embodiments, the scaffold can be configured to be delivered to the anastomotic site though the anastomosis itself or another opening made in the intestine. In such embodiments, the balloon catheter can be configured to be inflated centrally (i.e., approximately from the mid-point of the scaffold or even off center) as is shown in FIGS. 8a and 8b. In an embodiment of a deployment protocol using such an approach, the delivery catheter can inserted through anastomosis prior to closure of the anastomosis, then the surgeon sutures around the delivery catheter, the balloon is inflated to deploy the scaffold and then deflated and withdrawn through the remaining opening in the anastomosis. The surgeon can then make a final suture to close that remaining opening. In a variation, the surgeon could also at least partially inflate the balloon and expand the scaffold and thus used the scaffold as a mandrel or support to suture against (making the suturing process easier since the scaffold provides a structure to push against) or could actually place sutures or other closure element into the scaffold itself. This latter approach provides an additional means of retaining the scaffold at the anastomotic site and preventing scaffold migration.

Figure 9A:
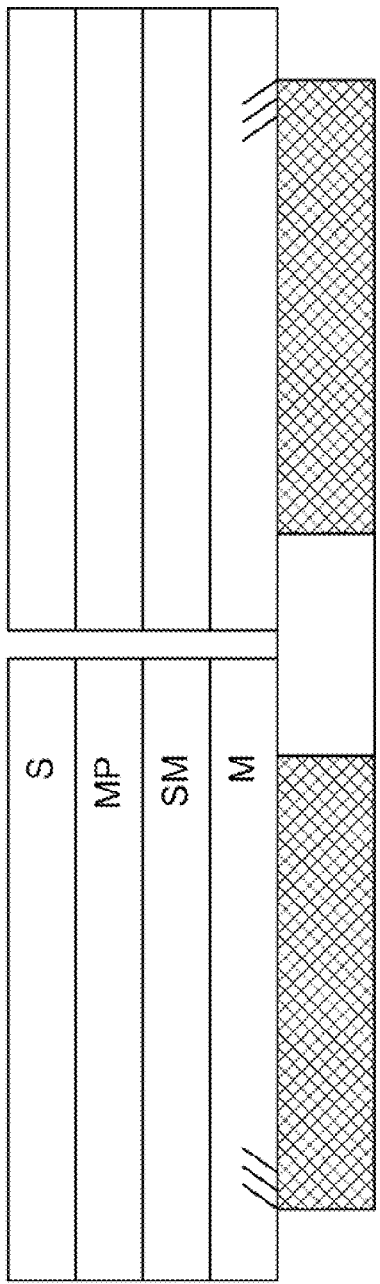
FIG. 9a is a cross sectional view illustrating positioning and attachment of the scaffold at the intestinal wall of the anastomotic site to place cut tissue layers in apposition.
Figure 9B:
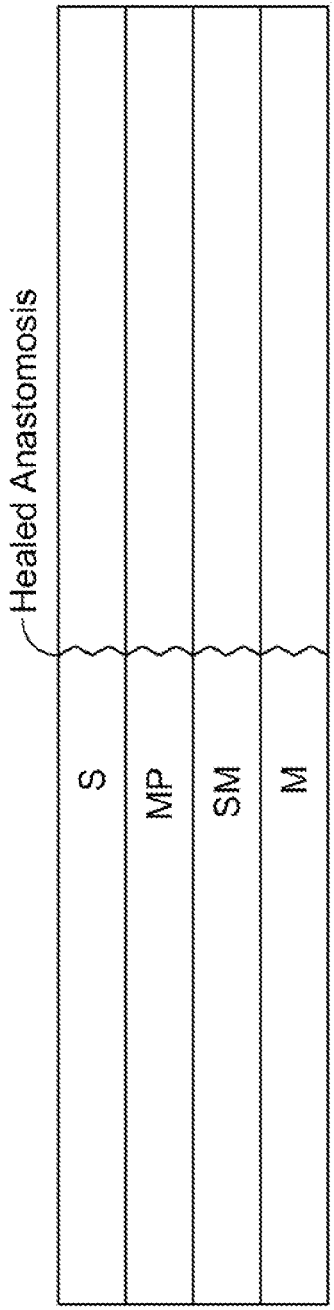
FIG. 9b is a cross sectional view illustrating the anastomotic site in a healed state with the tissue layers in alignment.

Referring now to FIGS. 9a-9b, a discussion will now be presented of the positioning of scaffold 10 at the anastomotic site AS to facilitate and promote the anastomotic healing process. Since many embodiments of the invention are configured for use in intestinal and other GI applications, a brief discussion will also be presented of structure of the morphology of the intestinal wall. The four major layers of the GI tract including the intestines (except for the extraperitoneal structures such as the esophagus and the lower third of the rectum) are shown in FIG. 9a. These layers include (1) the mucosa M, which consists of the epithelium, lamina propia and muscularis mucosa; (2) the submucosa, SM; (3) the muscularis propia MP, and (4) the serosa S, on the outer layer on the intestine. The thickness of the bowel wall BW is approximately 3 mm.

FIG. 9a shows a close-up view of the positioning of scaffold 10 on the surface BS of bowel wall BW over anastomosis A. Desirably, the scaffold is positioned on the bowel wall surface such that the center 12c of scaffold 10 and the center 50c of barrier layer 50 are approximately aligned with the anastomosis so that portions of barrier layer 50 lie on either side of the anastomosis (positioning can be facilitated by the use of radio-opaque or other imaging markers described herein). This facilitates the production of a good seal around the anastomosis and also serves to facilitate the healing of the anastomosis by having a biocompatible protective layer positioned immediately over the anastomosis to keep bacteria out of the anastomosis. It also serves to mechanically support and buttress the anastomosis and surrounding tissue while keeping them in some amount of compression. In this way, scaffold 10 serves both as a mechanical support and also a mechanical clamp. This support and clamp function in turn serves to keep opposing like tissue layers of the anastomosis (e.g., the serosa S) in apposition during the period of anastomotic healing allowing healing between like tissue layers. Healing proceeds faster between like tissue layers since cells from a layer on one side of the anastomosis can readily in grow into a like tissue layer on the other side. Once the anastomosis has healed, as is shown in FIG. 9b, the wound edges are connected and the four intestinal layers are in proper alignment with like tissue having joined like tissue resulting in a stronger longer lasting anastomotic tissue juncture. In this way, scaffold 10 can serve both as a tissue alignment fixture and tissue healing platform.

Figure 10:
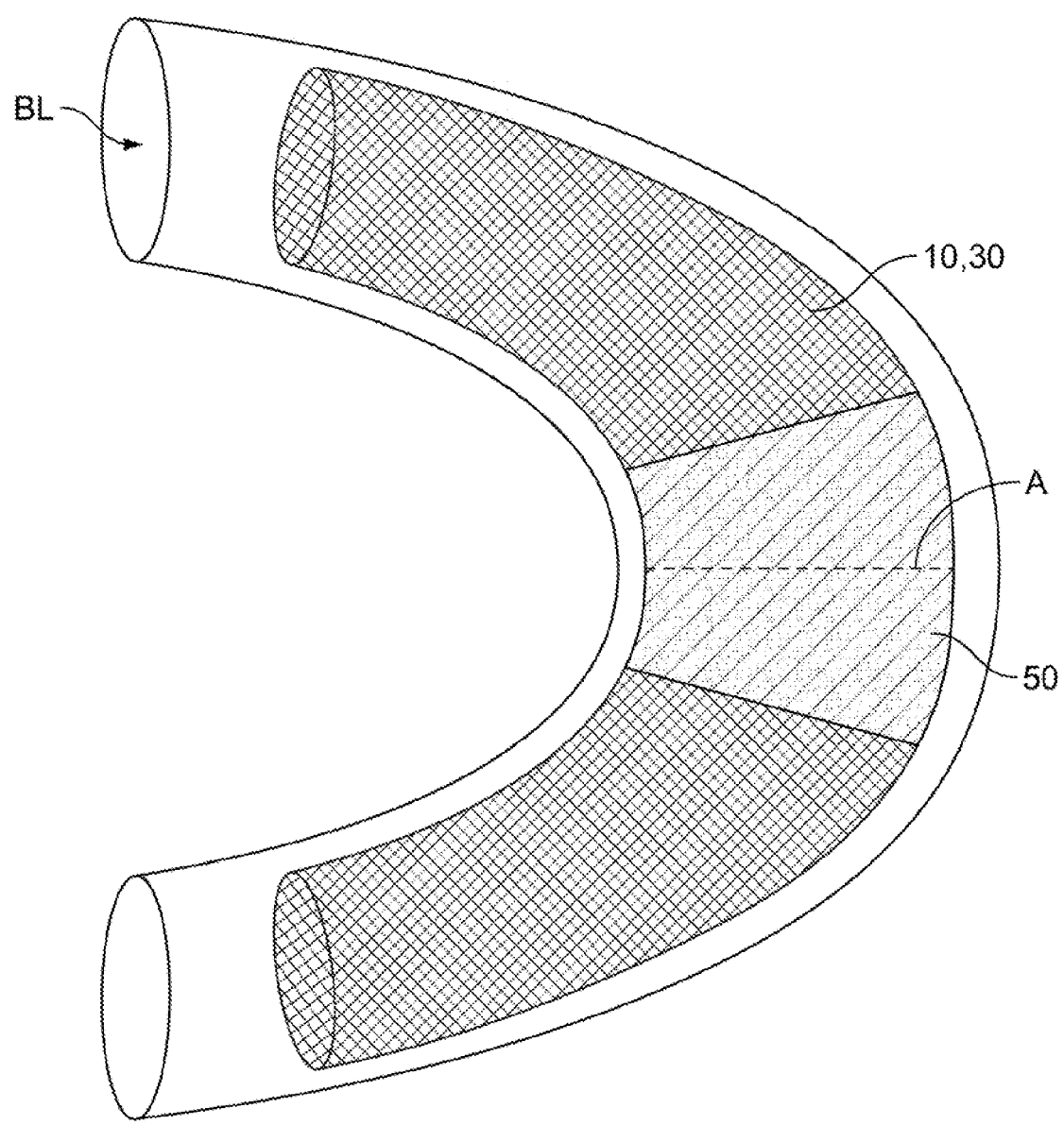
FIG. 10 illustrates an embodiment of a scaffold for use in an end-to-end anastomosis at anastomotic site having a curved body lumen.
Figure 11A:
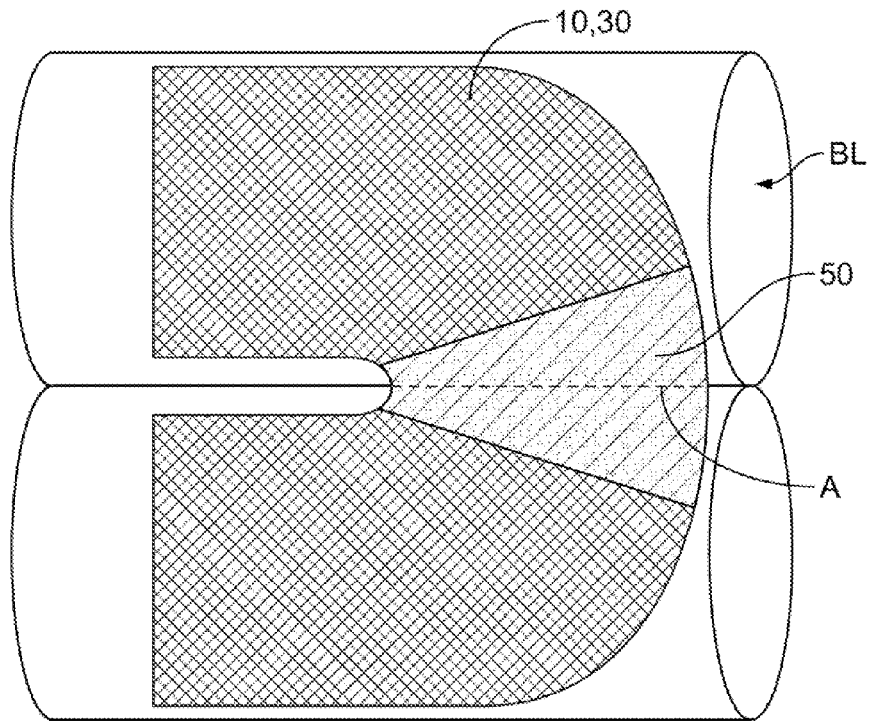
FIGS. 11a and 11b illustrate embodiments of a scaffold for use in side-to-side anastomoses for body lumens having varying alignments.
Figure 11B:
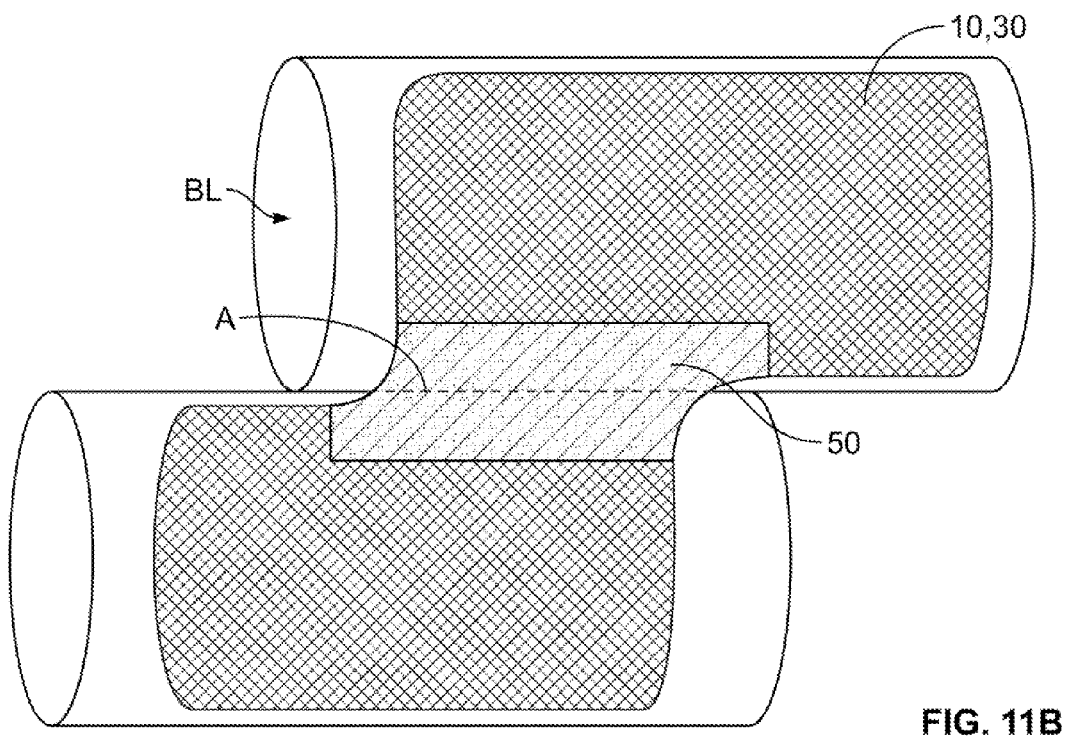
Figure 12:
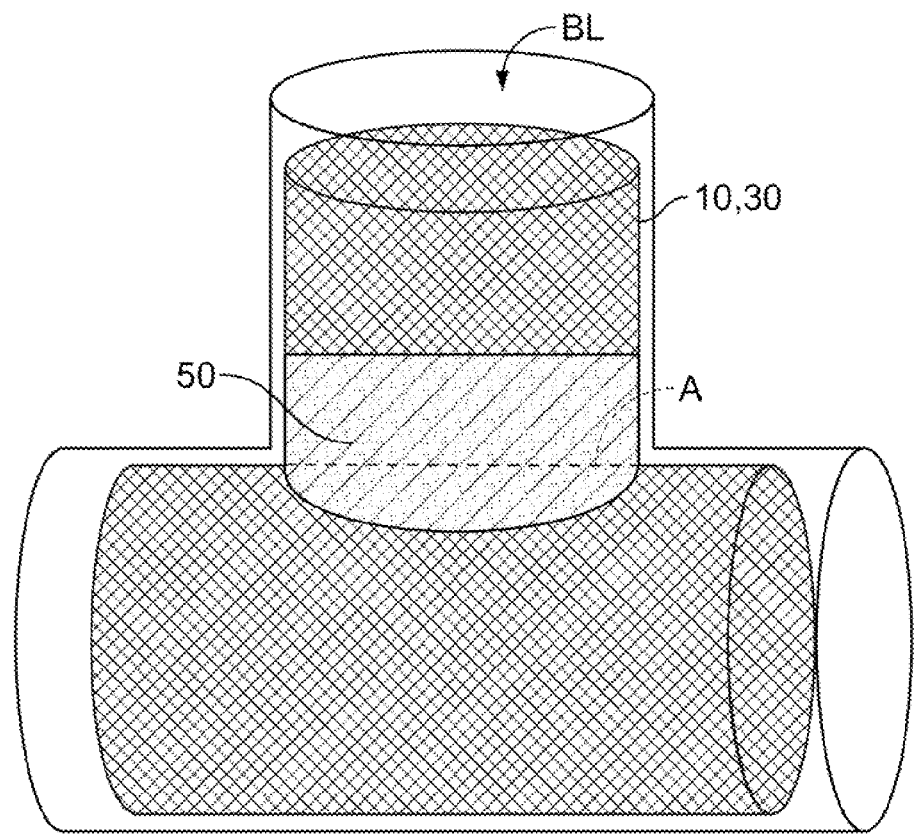
FIG. 12 illustrates an embodiment of a scaffold for use in a side-to-end anastomosis.
Figure 13:
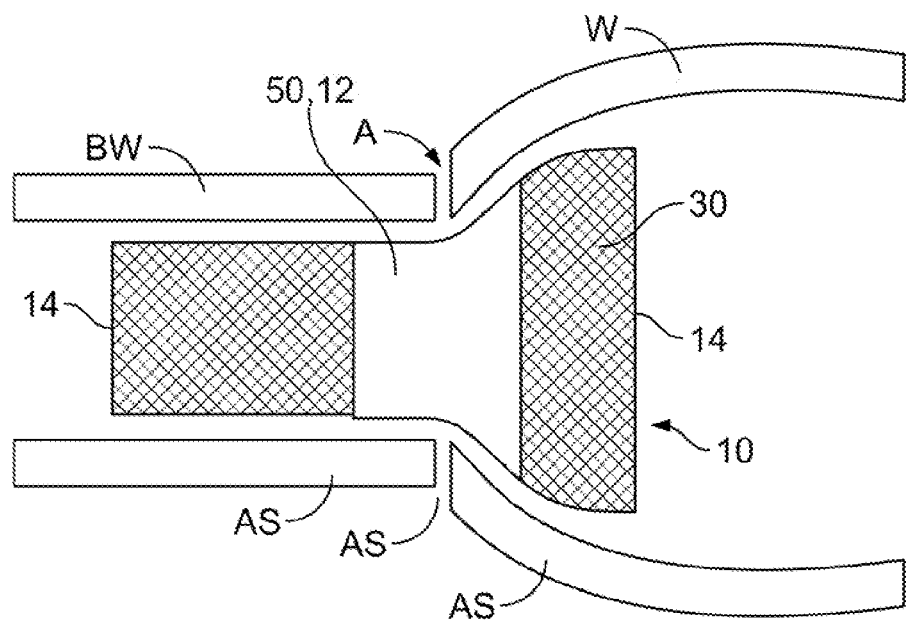
FIG. 13 illustrates an embodiment of a scaffold for use in an anastomosis between a larger and smaller diameter body lumen such as the stomach and small intestine.

Referring now to FIGS. 10-11a, 11b, 12 and 13, in many embodiments, scaffold 10 can be sufficiently conformable to conform to various shapes for a variety of anastomotic configurations such those shown in the respective figures. Likewise, the shape of protective member 51 can also be conformable. In many embodiments, the deployed state of the scaffold can have a cylindrical or tube-like shape for doing end-to-end anastomosis as is shown in FIGS. 1-2. Such embodiments can also sufficiently be conformable to conform to other shapes for doing other anastomotic configurations as well. Specific embodiments can be sufficiently flexible to bend and twist to conform to the curved, convoluted or other shape of a desired intestinal segment or other body lumen. Various embodiments of a cylindrical shaped scaffold can also be tapered to accommodate the taper of a particular body lumen (e.g. the rectum or sigmoid colon). In other specific embodiments, the deployed state of the scaffold can be curved for doing an end to end anastomosis, in a curved body lumen as shown in FIG. 10; approximately U-shaped for doing a side-to-side anastomosis with an aligned intestine (as is shown in FIG. 11a.), approximately S-shaped for doing a side-to-side anastomosis with an off-set intestine (as is shown in FIG. 11b.), or can be approximately T-shaped for doing a side-to-end anastomosis (as is shown in FIG. 12). In other embodiments, the scaffold can have a funnel or wine glass shape for doing anastomoses between a larger and smaller diameter body lumen (as is shown in FIG. 13) such as between the stomach and small intestine.

Accordingly, such embodiments are particularly useful for various gastric bypass procedures.

Other shapes for scaffold 10 are also contemplated including an inverted curve, i.e. a curve greater than about 180°. The particular shape can be adapted for the particular anastomosis and the anatomy of the selected lumen. The scaffold can be pre-shaped or can be shaped by the physician prior to insertion and then mounted onto the delivery catheter. For these and related embodiments, expansion of the scaffold using a balloon catheter can be done in one of several ways depending upon the anatomy of the selected lumen and configuration of the anastomosis. These include the following: i) using a single balloon; ii) using two balloons (using kissing balloon techniques known in the angioplasty arts) or ii) using multiple inflations from a single balloon that is moved in different locations through the prosthetic scaffold using methods described herein.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the prosthetic scaffold system and related methods and can be configured for positioning in and scaffolding of an anastomotic site in any number of body lumens such as those found in the esophagus, the heart (e.g. a coronary artery), the liver (e.g., the hepatic duct, the bilary tree etc.), the pancreas (e.g., the pancreatic duct), gall bladder (the cystic duct), the brain (e.g. a cerebral artery), the aorta, the carotid artery, the femoral or other peripheral artery or vein and like sites. The scaffold can be shaped, sized, coated and otherwise adapted for a delivery and deployment to the particular location. Also, embodiments of the system can be sized or otherwise adapted for various pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A tissue scaffold for placement at an anastomotic site within a gastrointestinal (GI) tract of a patient to promote healing of an anastomosis within the GI tract, the tissue scaffold comprising:
   a radially expandable scaffold structure including two lateral portions, a mid portion and at least one retention element coupled to each lateral portion, the at least one retention element configured to engage a tissue wall of the GI tract when the scaffold structure is expanded to retain the tissue scaffold at the anastomotic site during a period of anastomotic healing; and
   a barrier layer covering at least the mid portion, the barrier layer configured to engage a tissue wall of the anastomotic site by flexibly changing shape when the scaffold structure is expanded to provide a fluidic seal at opposing GI tissue layers of the anastomosis, the barrier layer having a length when the scaffold structure is fully expanded which extends laterally on either side of the mid portion so as to form and maintain the fluidic seal, the barrier layer and the scaffold structure having degradation rates configured such that after implantation, the barrier layer outlasts the scaffold structure;
   wherein the mid portion of the scaffold structure has a radial stiffness configured to form and maintain the seal at the anastomosis during a peristaltic contraction within the GI tract;
   wherein the mid portion of the scaffold structure has a greater radial stiffness than the lateral portions such that, when the scaffold structure is expanded, the lateral portions and retention elements engage the tissue wall of the GI tract prior to engagement by the mid portion including the barrier layer; and wherein radial expansion of the tissue scaffold causes the tissue scaffold to exert a compressive force on the anastomosis to maintain an alignment of opposing GI tissue layers of the anastomosis and prevent failure of the anastomosis from tensile forces caused by the peristaltic contraction within the GI tract.

2. The tissue scaffold of claim 1, wherein the barrier layer includes a biological material.

3. The tissue scaffold of claim 2, wherein the biological material includes at least one of a growth factor, VEGF, an anti-inflammatory agent or an antimicrobial agent.

4. The tissue scaffold of claim 1, wherein at least a portion of the tissue scaffold comprises a bio-resorbable material.

5. The tissue scaffold of claim 4, wherein the bio-resorbable material comprises polyglycolic acid, polylactic acid, or a blend of polyglycolic acid and polylactic acid.

6. The tissue scaffold of claim 1, wherein the scaffold structure comprises a plurality of axially adjacent cells.

7. The tissue scaffold of claim 1, wherein an axial length of the tissue scaffold shortens when the scaffold structure is expanded.

8. The tissue scaffold of claim 1, wherein the scaffold structure is expandable by one of an expandable device or an inflatable balloon.

9. The tissue scaffold of claim 1, wherein the barrier layer is positioned over the scaffold structure to extend laterally on either side of a center of the scaffold structure.

10. The tissue scaffold of claim 1, wherein when the scaffold structure is partially expanded, the scaffold structure has an outwardly flared shape with respect to a lateral axis of the scaffold structure.

11. The tissue scaffold of claim 1, wherein the barrier layer comprises a tubular member disposed over the scaffold structure.

12. The tissue scaffold of claim 1, wherein the barrier layer comprises one of a fluoropolymer, PTFE, polyethylene, PET or NYLON.

13. The tissue scaffold of claim 1, wherein the scaffold structure has sufficient flexibility to bend in conformity to a curve of the GI tract.

14. The tissue scaffold of claim 1, wherein the scaffold structure has a substantially tubular shape in an expanded state.

15. The tissue scaffold of claim 1, wherein the scaffold structure has a substantial T-shape in an expanded state, the shape configured to be positioned in an end to side anastomosis.

16. The tissue scaffold of claim 1, wherein the scaffold structure has a substantial S-shape in an expanded state, the shape configured to be positioned in a side to side anastomosis.

17. The tissue scaffold of claim 1, wherein the scaffold structure has a curved shape in an expanded state, the shape configured to be positioned in a curved body lumen.

18. The tissue scaffold of claim 1, wherein the retention element is a hook.

\* \* \* \* \*